(12) United States Patent
Zhang et al.

(10) Patent No.: US 10,717,753 B2
(45) Date of Patent: Jul. 21, 2020

(54) DEUTERIUM-MODIFIED BRIGATINIB DERIVATIVES, PHARMACEUTICAL COMPOSITIONS COMPRISING SAME, AND USE THEREOF

(71) Applicant: Chia Tai Tianqing Pharmaceutical Group Co., Ltd., Lianyungang (CN)

(72) Inventors: Yinsheng Zhang, Lianyungang (CN); Baomin Liu, Lianyungang (CN); Beibei Yang, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 15/778,897

(22) PCT Filed: Nov. 24, 2016

(86) PCT No.: PCT/CN2016/107048
§ 371 (c)(1),
(2) Date: May 24, 2018

(87) PCT Pub. No.: WO2017/088784
PCT Pub. Date: Jun. 1, 2017

(65) Prior Publication Data
US 2018/0346498 A1 Dec. 6, 2018

(30) Foreign Application Priority Data
Nov. 27, 2015 (CN) .......... 2015 1 0846894

(51) Int. Cl.
*C07F 9/6558* (2006.01)
*A61K 31/675* (2006.01)
*A61P 35/00* (2006.01)
*C07B 59/00* (2006.01)

(52) U.S. Cl.
CPC ........ *C07F 9/65583* (2013.01); *A61K 31/675* (2013.01); *A61P 35/00* (2018.01); *C07F 9/6558* (2013.01); *C07B 59/004* (2013.01)

(58) Field of Classification Search
CPC .. C07F 9/65583; C07F 9/6558; A61K 31/675; C07B 59/004
See application file for complete search history.

(56) References Cited

U.S. PATENT DOCUMENTS

| 9,809,572 B2 | 11/2017 | Lv |
| 2012/0202776 A1 | 8/2012 | Wang |
| 2014/0024620 A1 | 1/2014 | Dalgarno |
| 2015/0225436 A1 | 8/2015 | Wang |
| 2015/0299166 A1 | 10/2015 | Tung |

FOREIGN PATENT DOCUMENTS

| CN | 102105150 A | 6/2011 |
| CN | 103153064 A | 6/2013 |
| CN | 104109149 A | 10/2014 |
| CN | 106188138 A | 12/2016 |
| WO | WO 2011/146945 A2 | 11/2011 |
| WO | WO 2012/051587 A1 | 4/2012 |
| WO | WO 2014/173291 A1 | 10/2014 |

OTHER PUBLICATIONS

International Search Report in International Application No. PCT/CN2016/107048, dated Mar. 9, 2017 (7 pages w/English translation).
Written Opinion in International Application No. PCT/CN2016/107048, dated Mar. 9, 2017 (16 pages w/English translation).
Extended European Search Report for Application No. 16868007.2, dated Aug. 8, 2018 (9 pages).
Gras, J.; "Brigatinib. ALK and mutant EGFR inhibitor. Treatment of NSCLC"; Drugs of the Future, vol. 40, No. 5, p. 287; May 1, 2015: XP055494721; ISSN: 0377-8282 (6 pages).

*Primary Examiner* — Joseph R Kosack
(74) *Attorney, Agent, or Firm* — Nixon Peabody LLP

(57) ABSTRACT

The present invention relates to the field of pharmaceutical chemistry, and relates to a deuterium-modified Brigatinib derivative, preparation method thereof, pharmaceutical composition containing the same and the uses of the deuterium-modified Brigatinib derivative and the pharmaceutical composition thereof in preparing a medicament for treating the disease mediated by anaplastic lymphoma kinase. The deuterium-modified Brigatinib derivative of the present invention has an excellent inhibitory activity on anaplastic lymphoma kinase and has better pharmacodynamic or pharmacokinetic properties relative to Brigatinib.

10 Claims, No Drawings

DEUTERIUM-MODIFIED BRIGATINIB DERIVATIVES, PHARMACEUTICAL COMPOSITIONS COMPRISING SAME, AND USE THEREOF

REFERENCE TO RELATED APPLICATION

The present application is a U.S. national stage of PCT/CN2016/107048 filed on Nov. 24, 2016, which claims the benefit of Chinese invention patent application No. 201510846894.0 filed on Nov. 27, 2015 in the State Intellectual Property Office of the P. R. China.

TECHNICAL FIELD

The present invention belongs to the field of pharmaceutical chemistry, and relates to a deuterium-modified Brigatinib derivative, a preparation method thereof, a pharmaceutical composition comprising the deuterium-modified Brigatinib derivative and a use of the deuterium-modified Brigatinib derivative and a pharmaceutical composition thereof for the preparation of a treatment for diseases mediated by anaplastic lymphoma kinases.

BACKGROUND

Brigatinib, with a chemical name of 5-chloro-$N^4$-[2-(dimethylphosphonyl)phenyl]-$N^2$-{2-methoxy-4-[4-(4-methylpiperazin-1-yl)piperidin-1-yl]phenyl}pyrimidine-2,4-diamine, is an anaplastic lymphoma kinase (AKL) inhibitor developed by ARIAD Pharmaceuticals, Inc, which can also inhibit EGFR and c-ros oncogene 1 (ROS1), and it thus can be used for treating ALK-positive non-small cell lung cancer and is currently in Phase II clinical trials. In October 2014, the US FDA granted its breakthrough therapeutic drug qualification. The results from Phase I/II clinical trials show that Brigatinib has persistent anti-tumor activity in patients with ALK-positive non-small cell lung cancer (including those with brain metastases).

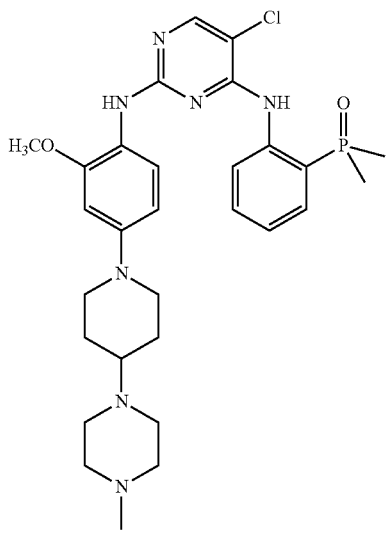 [SMILES: COc1cc(N2CCC(N3CCN(C)CC3)CC2)ccc1Nc1ncc(Cl)c(Nc2ccccc2P(C)(C)=O)n1]

Poor properties of absorption, distribution, metabolism and/or excretion (ADME) have been known as main reasons for failure of clinical trials of numerous drug candidates. The application ranges of many drugs currently on the market have been also limited due to their poor ADME properties. Rapid metabolism of drugs will cause many drugs, which could have treated diseases with high efficient, difficult to be prepared into medicine, due to excessively rapid metabolism and clearance from the body. Although the problem of the rapid clearance of drugs may be solved by frequent or high-dose administration, such approaches may present several problems, such as poor patient compliance, side effects caused by high-dose administration, increased therapy costs and the like. Furthermore, rapidly metabolized drugs may also expose patients to adverse toxicity or reactive metabolites.

Although Brigatinib as an inhibitor of ALK can effectively treat ALK-positive non-small cell lung cancer, it is still challenging to develop a novel compound which can treat ALK-positive non-small cell lung cancer and has good oral bioavailability and druggability. Therefore, there still is a need for the development of a compound suitable as a therapeutic agent with selective inhibition activity for anaplastic lymphoma kinase (AKL) or having better pharmacodynamics/pharmacokinetics in the art. The present invention provides such compounds.

SUMMARY OF THE INVENTION

The present invention provides a compound represented by Formula I, or a pharmaceutically acceptable salt, solvate or prodrug thereof:

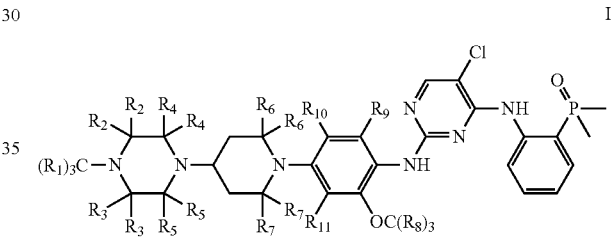

wherein $R_1$, $R_2$, $R_3$, $R_4$, $R_5$, $R_6$, $R_7$, $R_8$, $R_9$, $R_{10}$ and $R_{11}$ are each independently selected from hydrogen (H) or deuterium (D),
provided that at least one of $R_1$, $R_2$, $R_3$, $R_4$, $R_5$, $R_6$, $R_7$, $R_8$, $R_9$, $R_{10}$ and $R_{11}$ is selected from deuterium.

In an aspect, the present invention provides a compound represented by Formula I, or a pharmaceutically acceptable salt, solvate or prodrug thereof:

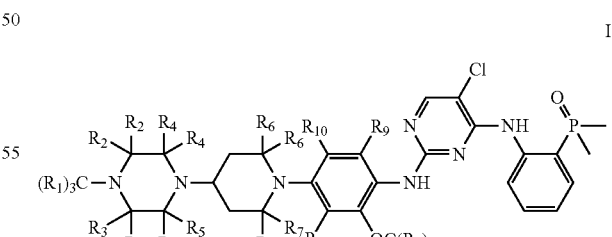

wherein $R_1$, $R_2$, $R_3$, $R_4$, $R_5$, $R_6$, $R_7$, $R_8$, $R_9$, $R_{10}$ and $R_{11}$ are each independently selected from hydrogen (H) or deuterium (D);
provided that at least one of $R_1$, $R_2$, $R_3$, $R_4$, $R_5$, $R_6$, $R_7$, $R_8$, $R_9$, $R_{10}$ and $R_{11}$ is selected from deuterium.

It will be appreciated that, when $R_1$ is selected from hydrogen or deuterium, the corresponding structural unit $(R_1)_3C-$ in the compound of Formula I is $-CH_3$ or $-CD_3$; and when $R_8$ is selected from hydrogen or deuterium, the corresponding structural unit $-OC(R_8)_3$ in the compound of Formula I is $-OCH_3$ or $-OCD_3$.

It will be appreciated that, the two $R_2$ in the compound of formula I are identical, that is, when one of them is hydrogen or deuterium, the other one is correspondingly hydrogen or deuterium; the same understanding should be applied to $R_3$, $R_4$, $R_5$, $R_6$ and $R_7$.

In some embodiments of the present invention, $R_1$ is selected from deuterium, and $R_2$, $R_3$, $R_4$, $R_5$, $R_6$, $R_7$, $R_8$, $R_9$, $R_{10}$ and $R_{11}$ are each independently selected from hydrogen or deuterium.

In some embodiments of the present invention, $R_1$ is selected from deuterium, $R_2$, $R_3$, $R_4$, $R_5$, $R_6$, $R_7$, $R_8$, $R_9$, $R_{10}$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_1$ is selected from deuterium, $R_8$ is selected from hydrogen, and $R_2$, $R_3$, $R_4$, $R_5$, $R_6$, $R_7$, $R_9$, $R_{10}$ and $R_{11}$ are each independently selected from hydrogen or deuterium.

In some embodiments of the present invention, $R_1$ is selected from deuterium, $R_8$ is selected from hydrogen, $R_2$, $R_3$, $R_4$, $R_5$, $R_6$, $R_7$, $R_9$, $R_{10}$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_1$ is selected from deuterium, $R_8$, $R_9$, $R_{10}$ and $R_{11}$ are selected from hydrogen, and $R_2$, $R_3$, $R_4$, $R_5$, $R_6$ and $R_7$ are each independently selected from hydrogen or deuterium.

In some embodiments of the present invention, $R_1$ is selected from deuterium, $R_8$, $R_9$, $R_{10}$ and $R_{11}$ are selected from hydrogen, $R_2$, $R_3$, $R_4$, $R_5$, $R_6$ and $R_7$ are each independently selected from hydrogen or deuterium, and $R_2$ is identical to $R_3$, $R_4$ is identical to $R_5$, $R_6$ is identical to $R_7$.

In some embodiments of the present invention, $R_1$ is selected from deuterium, $R_6$, $R_7$, $R_8$, $R_9$, $R_{10}$ and $R_{11}$ are selected from hydrogen, and $R_2$, $R_3$, $R_4$ and $R_5$ are each independently selected from hydrogen or deuterium.

In some embodiments of the present invention, $R_1$ is selected from deuterium, $R_6$, $R_7$, $R_8$, $R_9$, $R_{10}$ and $R_{11}$ are selected from hydrogen, $R_2$, $R_3$, $R_4$ and $R_5$ are each independently selected from hydrogen or deuterium, and $R_2$ is identical to $R_3$, $R_4$ is identical to $R_5$. In some embodiments of the present invention, $R_1$ is selected from deuterium, $R_4$, $R_5$, $R_6$, $R_7$, $R_8$, $R_9$, $R_{10}$ and $R_{11}$ are selected from hydrogen, and $R_2$ and $R_3$ are each independently selected from hydrogen or deuterium.

In some embodiments of the present invention, $R_1$ is selected from deuterium, $R_4$, $R_5$, $R_6$, $R_7$, $R_8$, $R_9$, $R_{10}$ and $R_{11}$ are selected from hydrogen, $R_2$ and $R_3$ are each independently selected from hydrogen or deuterium, and $R_2$ is identical to $R_3$.

In some embodiments of the present invention, $R_2$ and $R_3$ are selected from deuterium, and $R_1$, $R_4$, $R_5$, $R_6$, $R_7$, $R_8$, $R_9$, $R_{10}$ and $R_{11}$ are each independently selected from hydrogen or deuterium.

In some embodiments of the present invention, $R_2$ and $R_3$ are selected from deuterium, $R_1$, $R_4$, $R_5$, $R_6$, $R_7$, $R_8$, $R_9$, $R_{10}$ and $R_{11}$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_9$, $R_{10}$ and $R_{11}$ are selected from hydrogen, and $R_1$, $R_4$, $R_5$, $R_6$, $R_7$ and $R_8$ are each independently selected from hydrogen or deuterium.

In some embodiments of the present invention, $R_2$ and $R_3$ are selected from deuterium, $R_9$, $R_{10}$ and $R_{11}$ are selected from hydrogen, $R_1$, $R_4$, $R_5$, $R_6$, $R_7$ and $R_8$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_8$, $R_9$, $R_{10}$ and $R_{11}$ are selected from hydrogen, and $R_1$, $R_4$, $R_5$, $R_6$ and $R_7$ are each independently selected from hydrogen or deuterium.

In some embodiments of the present invention, $R_2$ and $R_3$ are selected from deuterium, $R_8$, $R_9$, $R_{10}$ and $R_{11}$ are selected from hydrogen, $R_1$, $R_4$, $R_5$, $R_6$ and $R_7$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_6$, $R_7$, $R_8$, $R_9$, $R_{10}$ and $R_{11}$ are selected from hydrogen, and $R_1$, $R_4$ and $R_5$ are each independently selected from hydrogen or deuterium.

In some embodiments of the present invention, $R_2$ and $R_3$ are selected from deuterium, $R_6$, $R_7$, $R_8$, $R_9$, $R_{10}$ and $R_{11}$ are selected from hydrogen, $R_1$, $R_4$ and $R_5$ are each independently selected from hydrogen or deuterium, and $R_4$ is identical to $R_5$.

In some embodiments of the present invention, $R_2$ and $R_3$ are selected from deuterium, $R_1$ is selected from hydrogen, and $R_4$, $R_5$, $R_6$, $R_7$, $R_8$, $R_9$, $R_{10}$ and $R_{11}$ are each independently selected from hydrogen or deuterium.

In some embodiments of the present invention, $R_2$ and $R_3$ are selected from deuterium, $R_1$ is selected from hydrogen, $R_4$, $R_5$, $R_6$, $R_7$, $R_8$, $R_9$, $R_{10}$ and $R_{11}$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_1$, $R_9$, $R_{10}$ and $R_{11}$ are selected from hydrogen, and $R_4$, $R_5$, $R_6$, $R_7$ and $R_8$ are each independently selected from hydrogen or deuterium.

In some embodiments of the present invention, $R_2$ and $R_3$ are selected from deuterium, $R_1$, $R_9$, $R_{10}$ and $R_{11}$ are selected from hydrogen, $R_4$, $R_5$, $R_6$, $R_7$ and $R_8$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_1$, $R_8$, $R_9$, $R_{10}$ and $R_{11}$ are selected from hydrogen, and $R_4$, $R_5$, $R_6$ and $R_7$ are each independently selected from hydrogen or deuterium.

In some embodiments of the present invention, $R_2$ and $R_3$ are selected from deuterium, $R_1$, $R_8$, $R_9$, $R_{10}$ and $R_{11}$ are selected from hydrogen, $R_4$, $R_5$, $R_6$ and $R_7$ are each independently selected from hydrogen or deuterium, and $R_4$ is identical to $R_5$, $R_6$ is identical to $R_7$.

In some embodiments of the present invention, $R_2$ and $R_3$ are selected from deuterium, $R_1$, $R_6$, $R_7$, $R_8$, $R_9$, $R_{10}$ and $R_{11}$ are selected from hydrogen, and $R_4$ and $R_5$ are each independently selected from hydrogen or deuterium.

In some embodiments of the present invention, $R_2$ and $R_3$ are selected from deuterium, $R_1$, $R_6$, $R_7$, $R_8$, $R_9$, $R_{10}$ and $R_{11}$ are selected from hydrogen, $R_4$ and $R_5$ are each independently selected from hydrogen or deuterium, and $R_4$ is identical to $R_5$.

In some embodiments of the present invention, $R_1$, $R_2$ and $R_3$ are selected from deuterium, and $R_4$, $R_5$, $R_6$, $R_7$, $R_8$, $R_9$, $R_{10}$ and $R_{11}$ are each independently selected from hydrogen or deuterium.

In some embodiments of the present invention, $R_1$, $R_2$ and $R_3$ are selected from deuterium, $R_4$, $R_5$, $R_6$, $R_7$, $R_8$, $R_9$, $R_{10}$ and $R_{11}$ are each independently selected from hydrogen or deuterium, and $R_4$ is identical to $R_5$, $R_6$ is identical to $R_7$.

In some embodiments of the present invention, $R_1$, $R_2$ and $R_3$ are selected from deuterium, $R_8$ is selected from hydrogen, and $R_4$, $R_5$, $R_6$, $R_7$, $R_9$, $R_{10}$ and $R_{11}$ are each independently selected from hydrogen or deuterium.

In some embodiments of the present invention, $R_1$, $R_2$ and $R_3$ are selected from deuterium, $R_8$ is selected from hydrogen, $R_4$, $R_5$, $R_6$, $R_7$, $R_9$, $R_{10}$ and $R_{11}$ are each independently selected from hydrogen or deuterium, and $R_4$ is identical to $R_5$, $R_6$ is identical to $R_7$.

In some embodiments of the present invention, $R_1$, $R_2$ and $R_3$ are selected from deuterium, $R_8$, $R_9$, $R_{10}$ and $R_{11}$ are selected from hydrogen, and $R_4$, $R_5$, $R_6$ and $R_7$ are each independently selected from hydrogen or deuterium.

In some embodiments of the present invention, $R_1$, $R_2$ and $R_3$ are selected from deuterium, $R_8$, $R_9$, $R_{10}$ and $R_{11}$ are selected from hydrogen, $R_4$, $R_5$, $R_6$ and $R_7$ are each independently selected from hydrogen or deuterium, and $R_4$ is identical to $R_5$, $R_6$ is identical to $R_7$.

In some embodiments of the present invention, $R_1$, $R_2$ and $R_3$ are selected from deuterium, $R_6$, $R_7$, $R_8$, $R_9$, $R_{10}$ and $R_{11}$ are selected from hydrogen, and $R_4$ and $R_5$ are each independently selected from hydrogen or deuterium.

In some embodiments of the present invention, $R_1$, $R_2$ and $R_3$ are selected from deuterium, $R_6$, $R_7$, $R_8$, $R_9$, $R_{10}$ and $R_{11}$ are selected from hydrogen, $R_4$ and $R_5$ are each independently selected from hydrogen or deuterium, and $R_4$ is identical to $R_5$. In some embodiments of the present invention, $R_4$ and $R_5$ are selected from deuterium, and $R_1$, $R_2$, $R_3$, $R_6$, $R_7$, $R_8$, $R_9$, $R_{10}$ and $R_{11}$ are each independently selected from hydrogen or deuterium.

In some embodiments of the present invention, $R_4$ and $R_5$ are selected from deuterium, $R_1$, $R_2$, $R_3$, $R_6$, $R_7$, $R_8$, $R_9$, $R_{10}$ and $R_{11}$ are each independently selected from hydrogen or deuterium, and $R_2$ is identical to $R_3$, $R_6$ is identical to $R_7$.

In some embodiments of the present invention, $R_4$ and $R_5$ are selected from deuterium, $R_9$, $R_{10}$ and $R_{11}$ are selected from hydrogen, and $R_1$, $R_2$, $R_3$, $R_6$, $R_7$ and $R_8$ are each independently selected from hydrogen or deuterium.

In some embodiments of the present invention, $R_4$ and $R_5$ are selected from deuterium, $R_9$, $R_{10}$ and $R_{11}$ are selected from hydrogen, $R_1$, $R_2$, $R_3$, $R_6$, $R_7$ and $R_8$ are each independently selected from hydrogen or deuterium, and $R_2$ is identical to $R_3$, $R_6$ is identical to $R_7$.

In some embodiments of the present invention, $R_4$ and $R_5$ are selected from deuterium, $R_8$, $R_9$, $R_{10}$ and $R_{11}$ are selected from hydrogen, and $R_1$, $R_2$, $R_3$, $R_6$ and $R_7$ are each independently selected from hydrogen or deuterium.

In some embodiments of the present invention, $R_4$ and $R_5$ are selected from deuterium, $R_8$, $R_9$, $R_{10}$ and $R_{11}$ are selected from hydrogen, $R_1$, $R_2$, $R_3$, $R_6$ and $R_7$ are each independently selected from hydrogen or deuterium, and $R_2$ is identical to $R_3$, $R_6$ is identical to $R_7$.

In some embodiments of the present invention, $R_4$ and $R_5$ are selected from deuterium, $R_6$, $R_7$, $R_8$, $R_9$, $R_{10}$ and $R_{11}$ are selected from hydrogen, and $R_1$, $R_2$ and $R_3$ are each independently selected from hydrogen or deuterium.

In some embodiments of the present invention, $R_4$ and $R_5$ are selected from deuterium, $R_6$, $R_7$, $R_8$, $R_9$, $R_{10}$ and $R_{11}$ are selected from hydrogen, $R_1$, $R_2$ and $R_3$ are each independently selected from hydrogen or deuterium, and $R_2$ is identical to $R_3$.

In some embodiments of the present invention, $R_4$ and $R_5$ are selected from deuterium, $R_1$, $R_6$, $R_7$, $R_8$, $R_9$, $R_{10}$ and $R_{11}$ are selected from hydrogen, and $R_2$ and $R_3$ are each independently selected from hydrogen or deuterium.

In some embodiments of the present invention, $R_4$ and $R_5$ are selected from deuterium, $R_1$, $R_6$, $R_7$, $R_8$, $R_9$, $R_{10}$ and $R_{11}$ are selected from hydrogen, $R_2$ and $R_3$ are each independently selected from hydrogen or deuterium, and $R_2$ is identical to $R_3$.

In some embodiments of the present invention, $R_4$ and $R_5$ are selected from deuterium, $R_1$, $R_2$, $R_3$, $R_6$, $R_7$, $R_8$, $R_9$, $R_{10}$ and $R_{11}$ are each selected from hydrogen or deuterium, and not all $R_1$, $R_2$, $R_3$, $R_6$, $R_7$, $R_8$, $R_9$, $R_{10}$ and $R_{11}$ are hydrogen.

In some embodiments of the present invention, $R_4$ and $R_5$ are selected from deuterium, $R_1$, $R_2$, $R_3$, $R_6$, $R_7$, $R_8$, $R_9$, $R_{10}$ and $R_{11}$ are each independently selected from hydrogen or deuterium, not all $R_1$, $R_2$, $R_3$, $R_6$, $R_7$, $R_8$, $R_9$, $R_{10}$ and $R_{11}$ are hydrogen, $R_2$ is identical to $R_3$, and $R_6$ is identical to $R_7$.

In some embodiments of the present invention, $R_2$, $R_3$, $R_4$ and $R_5$ are selected from deuterium, and $R_1$, $R_6$, $R_7$, $R_8$, $R_9$, $R_{10}$ and $R_{11}$ are each independently selected from hydrogen or deuterium.

In some embodiments of the present invention, $R_2$, $R_3$, $R_4$ and $R_5$ are selected from deuterium, $R_1$, $R_6$, $R_7$, $R_8$, $R_9$, $R_{10}$ and $R_{11}$ are each independently selected from hydrogen or deuterium, and $R_6$ is identical to $R_7$.

In some embodiments of the present invention, $R_2$, $R_3$, $R_4$ and $R_5$ are selected from deuterium, $R_9$, $R_{10}$ and $R_{11}$ are selected from hydrogen, and $R_1$, $R_6$, $R_7$ and $R_8$ are each independently selected from hydrogen or deuterium.

In some embodiments of the present invention, $R_2$, $R_3$, $R_4$ and $R_5$ are selected from deuterium, $R_9$, $R_{10}$ and $R_{11}$ are selected from hydrogen, $R_1$, $R_6$, $R_7$ and $R_8$ are each independently selected from hydrogen or deuterium, and $R_6$ is identical to $R_7$.

In some embodiments of the present invention, $R_2$, $R_3$, $R_4$ and $R_5$ are selected from deuterium, $R_8$, $R_9$, $R_{10}$ and $R_{11}$ are selected from hydrogen, and $R_1$, $R_6$ and $R_7$ are each independently selected from hydrogen or deuterium.

In some embodiments of the present invention, $R_2$, $R_3$, $R_4$ and $R_5$ are selected from deuterium, $R_8$, $R_9$, $R_{10}$ and $R_{11}$ are selected from hydrogen, $R_1$, $R_6$ and $R_7$ are each independently selected from hydrogen or deuterium, and $R_6$ is identical to $R_7$.

In some embodiments of the present invention, $R_2$, $R_3$, $R_4$ and $R_5$ are selected from deuterium, $R_6$, $R_7$, $R_8$, $R_9$, $R_{10}$ and $R_{11}$ are selected from hydrogen, and $R_1$ is selected from hydrogen or deuterium.

In some embodiments of the present invention, $R_2$, $R_3$, $R_4$ and $R_5$ are selected from deuterium, $R_1$ is selected from hydrogen, and $R_6$, $R_7$, $R_8$, $R_9$, $R_{10}$ and $R_{11}$ are each independently selected from hydrogen or deuterium.

In some embodiments of the present invention, $R_2$, $R_3$, $R_4$ and $R_5$ are selected from deuterium, $R_1$ is selected from hydrogen, $R_6$, $R_7$, $R_8$, $R_9$, $R_{10}$ and $R_{11}$ are each independently selected from hydrogen or deuterium, and $R_6$ is identical to $R_7$.

In some embodiments of the present invention, $R_2$, $R_3$, $R_4$ and $R_5$ are selected from deuterium, $R_1$, $R_9$, $R_{10}$ and $R_{11}$ are selected from hydrogen, and $R_6$, $R_7$ and $R_8$ are each independently selected from hydrogen or deuterium.

In some embodiments of the present invention, $R_2$, $R_3$, $R_4$ and $R_5$ are selected from deuterium, $R_1$, $R_9$, $R_{10}$ and $R_{11}$ are selected from hydrogen, $R_6$, $R_7$ and $R_8$ are each independently selected from hydrogen or deuterium, and $R_6$ is identical to $R_7$.

In some embodiments of the present invention, $R_1$, $R_2$, $R_3$, $R_4$ and $R_5$ are selected from deuterium, and $R_6$, $R_7$, $R_8$, $R_9$, $R_{10}$ and $R_{11}$ are each independently selected from hydrogen or deuterium.

In some embodiments of the present invention, $R_1$, $R_2$, $R_3$, $R_4$ and $R_5$ are selected from deuterium, $R_6$, $R_7$, $R_8$, $R_9$, $R_{10}$ and $R_{11}$ are each independently selected from hydrogen or deuterium, and $R_6$ is identical to $R_7$.

In some embodiments of the present invention, $R_1$, $R_2$, $R_3$, $R_4$ and $R_5$ are selected from deuterium, $R_9$, $R_{10}$ and $R_{11}$ are selected from hydrogen, and $R_6$, $R_7$ and $R_8$ are each independently selected from hydrogen or deuterium.

In some embodiments of the present invention, $R_1$, $R_2$, $R_3$, $R_4$ and $R_5$ are selected from deuterium, $R_9$, $R_{10}$ and $R_{11}$ are selected from hydrogen, $R_6$, $R_7$ and $R_8$ are each independently selected from hydrogen or deuterium, and $R_6$ is identical to $R_7$.

In some embodiments of the present invention, $R_1$, $R_2$, $R_3$, $R_4$ and $R_5$ are selected from deuterium, $R_8$, $R_9$, $R_{10}$ and $R_{11}$ are selected from hydrogen, and $R_6$ and $R_7$ are each independently selected from hydrogen or deuterium.

In some embodiments of the present invention, $R_1$, $R_2$, $R_3$, $R_4$ and $R_5$ are selected from deuterium, $R_8$, $R_9$, $R_{10}$ and $R_{11}$ are selected from hydrogen, and $R_6$ and $R_7$ are each independently selected from hydrogen or deuterium, and $R_6$ is identical to $R_7$.

In some embodiments of the present invention, $R_6$ and $R_7$ are selected from deuterium, and $R_1$, $R_2$, $R_3$, $R_4$, $R_5$, $R_8$, $R_9$, $R_{10}$ and $R_{11}$ are each independently selected from hydrogen or deuterium.

In some embodiments of the present invention, $R_6$ and $R_7$ are selected from deuterium, $R_1$, $R_2$, $R_3$, $R_4$, $R_5$, $R_8$, $R_9$, $R_{10}$ and $R_{11}$ are each independently selected from hydrogen or deuterium, and $R_2$ is identical to $R_3$, $R_4$ is identical to $R_5$.

In some embodiments of the present invention, $R_6$ and $R_7$ are selected from deuterium, $R_9$, $R_{10}$ and $R_{11}$ are selected from hydrogen, and $R_1$, $R_2$, $R_3$, $R_4$, $R_5$ and $R_8$ are each independently selected from hydrogen or deuterium.

In some embodiments of the present invention, $R_6$ and $R_7$ are selected from deuterium, $R_9$, $R_{10}$ and $R_{11}$ are selected from hydrogen, and $R_1$, $R_2$, $R_3$, $R_4$, $R_5$ and $R_8$ are each independently selected from hydrogen or deuterium, and $R_2$ is identical to $R_3$, $R_4$ is identical to $R_5$.

In some embodiments of the present invention, $R_6$ and $R_7$ are selected from deuterium, $R_8$, $R_9$, $R_{10}$ and $R_{11}$ are selected from hydrogen, and $R_1$, $R_2$, $R_3$, $R_4$ and $R_5$ are each independently selected from hydrogen or deuterium.

In some embodiments of the present invention, $R_6$ and $R_7$ are selected from deuterium, $R_8$, $R_9$, $R_{10}$ and $R_{11}$ are selected from hydrogen, $R_1$, $R_2$, $R_3$, $R_4$ and $R_5$ are each independently selected from hydrogen or deuterium, and $R_2$ is identical to $R_3$, $R_4$ is identical to $R_5$.

In some embodiments of the present invention, $R_6$ and $R_7$ are selected from deuterium, $R_1$, $R_8$, $R_9$, $R_{10}$ and $R_{11}$ are selected from hydrogen, and $R_2$, $R_3$, $R_4$ and $R_5$ are each independently selected from hydrogen or deuterium.

In some embodiments of the present invention, $R_6$ and $R_7$ are selected from deuterium, $R_1$, $R_8$, $R_9$, $R_{10}$ and $R_{11}$ are selected from hydrogen, $R_2$, $R_3$, $R_4$ and $R_5$ are each independently selected from hydrogen or deuterium, and $R_2$ is identical to $R_3$, $R_4$ is identical to $R_5$.

In some embodiments of the present invention, $R_6$, $R_7$ and $R_8$ are selected from deuterium, and $R_1$, $R_2$, $R_3$, $R_4$, $R_5$, $R_9$, $R_{10}$ and $R_{11}$ are each independently selected from hydrogen or deuterium.

In some embodiments of the present invention, $R_6$, $R_7$ and $R_8$ are selected from deuterium, $R_1$, $R_2$, $R_3$, $R_4$, $R_5$, $R_9$, $R_{10}$ and $R_{11}$ are each independently selected from hydrogen or deuterium, and $R_2$ is identical to $R_3$, $R_4$ is identical to $R_5$.

In some embodiments of the present invention, $R_6$, $R_7$ and $R_8$ are selected from deuterium, $R_1$ is selected from hydrogen, and $R_2$, $R_3$, $R_4$, $R_5$, $R_9$, $R_{10}$ and $R_{11}$ are each independently selected from hydrogen or deuterium.

In some embodiments of the present invention, $R_6$, $R_7$ and $R_8$ are selected from deuterium, $R_1$ is selected from hydrogen, $R_2$, $R_3$, $R_4$, $R_5$, $R_9$, $R_{10}$ and $R_{11}$ are each independently selected from hydrogen or deuterium, and $R_2$ is identical to $R_3$, $R_4$ is identical to $R_5$.

In some embodiments of the present invention, $R_6$, $R_7$ and $R_8$ are selected from deuterium, $R_1$, $R_9$, $R_{10}$ and $R_{11}$ are selected from hydrogen, and $R_2$, $R_3$, $R_4$ and $R_5$ are each independently selected from hydrogen or deuterium.

In some embodiments of the present invention, $R_6$, $R_7$ and $R_8$ are selected from deuterium, $R_1$, $R_9$, $R_{10}$ and $R_{11}$ are selected from hydrogen, $R_2$, $R_3$, $R_4$ and $R_5$ are each independently selected from hydrogen or deuterium, and $R_2$ is identical to $R_3$, $R_4$ is identical to $R_5$.

In some embodiments of the present invention, $R_8$ is selected from deuterium, and $R_1$, $R_2$, $R_3$, $R_4$, $R_5$, $R_6$, $R_7$, $R_9$, $R_{10}$ and $R_{11}$ are each independently selected from hydrogen or deuterium.

In some embodiments of the present invention, $R_8$ is selected from deuterium, and $R_1$, $R_2$, $R_3$, $R_4$, $R_5$, $R_6$, $R_7$, $R_9$, $R_{10}$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_8$ is selected from deuterium, $R_6$, $R_7$, $R_9$, $R_{10}$ and $R_{11}$ are selected from hydrogen, and $R_1$, $R_2$, $R_3$, $R_4$ and $R_5$ are each independently selected from hydrogen or deuterium.

In some embodiments of the present invention, $R_8$ is selected from deuterium, $R_6$, $R_7$, $R_9$, $R_{10}$ and $R_{11}$ are selected from hydrogen, $R_1$, $R_2$, $R_3$, $R_4$ and $R_5$ are each independently selected from hydrogen or deuterium, and $R_2$ is identical to $R_3$, $R_4$ is identical to $R_5$.

In some embodiments of the present invention, $R_8$ is selected from deuterium, $R_1$ is selected from hydrogen, and $R_2$, $R_3$, $R_4$, $R_5$, $R_6$, $R_7$, $R_9$, $R_{10}$ and $R_{11}$ are each independently selected from hydrogen or deuterium.

In some embodiments of the present invention, $R_8$ is selected from deuterium, $R_1$ is selected from hydrogen, and $R_2$, $R_3$, $R_4$, $R_5$, $R_6$, $R_7$, $R_9$, $R_{10}$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_8$ is selected from deuterium, $R_1$, $R_9$, $R_{10}$ and $R_{11}$ are selected from hydrogen, and $R_2$, $R_3$, $R_4$, $R_5$, $R_6$ and $R_7$ are each independently selected from hydrogen or deuterium.

In some embodiments of the present invention, $R_8$ is selected from deuterium, $R_1$, $R_9$, $R_{10}$ and $R_{11}$ are selected from hydrogen, $R_2$, $R_3$, $R_4$, $R_5$, $R_6$ and $R_7$ are each independently selected from hydrogen or deuterium, and $R_2$ is identical to $R_3$, $R_4$ is identical to $R_5$, $R_6$ is identical to $R_7$.

In some embodiments of the present invention, $R_8$ is selected from deuterium, $R_1$, $R_6$, $R_7$, $R_9$, $R_{10}$ and $R_{11}$ are selected from hydrogen, and $R_2$, $R_3$, $R_4$ and $R_5$ are each independently selected from hydrogen or deuterium.

In some embodiments of the present invention, $R_8$ is selected from deuterium, $R_1$, $R_6$, $R_7$, $R_9$, $R_{10}$ and $R_{11}$ are selected from hydrogen, and $R_2$, $R_3$, $R_4$ and $R_5$ are each independently selected from hydrogen or deuterium, and $R_2$ is identical to $R_3$, $R_4$ is identical to $R_5$. In some embodiments of the present invention, $R_9$ and $R_{10}$ are selected from deuterium, and $R_1$, $R_2$, $R_3$, $R_4$, $R_5$, $R_6$, $R_7$, $R_8$ and $R_{11}$ are each independently selected from hydrogen or deuterium.

In some embodiments of the present invention, $R_9$ and $R_{10}$ are selected from deuterium, and $R_1$, $R_2$, $R_3$, $R_4$, $R_5$, $R_6$, $R_7$, $R_8$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_{11}$ is selected from deuterium, and $R_1$, $R_2$, $R_3$, $R_4$, $R_5$, $R_6$, $R_7$, $R_8$, $R_9$ and $R_{10}$ are each independently selected from hydrogen or deuterium.

In some embodiments of the present invention, $R_{11}$ is selected from deuterium, and $R_1$, $R_2$, $R_3$, $R_4$, $R_5$, $R_6$, $R_7$, $R_8$, $R_9$ and $R_{10}$ are each independently selected from hydrogen or deuterium, and $R_2$ is identical to $R_3$, $R_4$ is identical to $R_5$, $R_6$ is identical to $R_7$.

In some embodiments of the present invention, $R_{10}$ and $R_{11}$ are selected from deuterium, and $R_1$, $R_2$, $R_3$, $R_4$, $R_5$, $R_6$, $R_7$, $R_8$ and $R_9$ are each independently selected from hydrogen or deuterium.

In some embodiments of the present invention, $R_{10}$ and $R_{11}$ are selected from deuterium, and $R_1$, $R_2$, $R_3$, $R_4$, $R_5$, $R_6$, $R_7$, $R_8$ and $R_9$ are each independently selected from hydrogen or deuterium, and $R_2$ is identical to $R_3$, $R_4$ is identical to $R_5$, $R_6$ is identical to $R_7$.

In some embodiments of the present invention, $R_{10}$ and $R_{11}$ are selected from deuterium, $R_9$ is selected from hydrogen, and $R_1$, $R_2$, $R_3$, $R_4$, $R_5$, $R_6$, $R_7$ and $R_8$ are each independently selected from hydrogen or deuterium.

In some embodiments of the present invention, $R_{10}$ and $R_{11}$ are selected from deuterium, $R_9$ is selected from hydrogen, $R_1$, $R_2$, $R_3$, $R_4$, $R_5$, $R_6$, $R_7$ and $R_8$ are each independently selected from hydrogen or deuterium, and $R_2$ is identical to $R_3$, $R_4$ is identical to $R_5$, $R_6$ is identical to $R_7$.

In some embodiments of the present invention, $R_9$, $R_{10}$ and $R_{11}$ are selected from deuterium, and $R_1$, $R_2$, $R_3$, $R_4$, $R_5$, $R_6$, $R_7$ and $R_8$ are each independently selected from hydrogen or deuterium.

In some embodiments of the present invention, $R_9$, $R_{10}$ and $R_{11}$ are selected from deuterium, and $R_1$, $R_2$, $R_3$, $R_4$, $R_5$, $R_6$, $R_7$ and $R_8$ are each independently selected from hydrogen or deuterium, and $R_2$ is identical to $R_3$, $R_4$ is identical to $R_5$, $R_6$ is identical to $R_7$.

In some embodiments of the present invention, $R_1$ and $R_8$ are selected from deuterium, and $R_2$, $R_3$, $R_4$, $R_5$, $R_6$, $R_7$, $R_9$, $R_{10}$ and $R_{11}$ are each independently selected from hydrogen or deuterium.

In some embodiments of the present invention, $R_1$ and $R_8$ are selected from deuterium, and $R_2$, $R_3$, $R_4$, $R_5$, $R_6$, $R_7$, $R_9$, $R_{10}$ and $R_{11}$ are each independently selected from hydrogen or deuterium, and $R_2$ is identical to $R_3$, $R_4$ is identical to $R_5$, $R_6$ is identical to $R_7$.

In some embodiments of the present invention, $R_1$ and $R_8$ are selected from deuterium, $R_9$, $R_{10}$ and $R_{11}$ are selected from hydrogen, and $R_2$, $R_3$, $R_4$, $R_5$, $R_6$ and $R_7$ are each independently selected from hydrogen or deuterium.

In some embodiments of the present invention, $R_1$ and $R_8$ are selected from deuterium, $R_9$, $R_{10}$ and $R_{11}$ are selected from hydrogen, and $R_2$, $R_3$, $R_4$, $R_5$, $R_6$ and $R_7$ are each independently selected from hydrogen or deuterium, and $R_2$ is identical to $R_3$, $R_4$ is identical to $R_5$, $R_6$ is identical to $R_7$.

In some embodiments of the present invention, $R_1$ and $R_8$ are selected from deuterium, $R_6$, $R_7$, $R_9$, $R_{10}$ and $R_{11}$ are selected from hydrogen, and $R_2$, $R_3$, $R_4$ and $R_5$ are each independently selected from hydrogen or deuterium.

In some embodiments of the present invention, $R_1$ and $R_8$ are selected from deuterium, $R_6$, $R_7$, $R_9$, $R_{10}$ and $R_{11}$ are selected from hydrogen, and $R_2$, $R_3$, $R_4$ and $R_5$ are each independently selected from hydrogen or deuterium, and $R_2$ is identical to $R_3$, $R_4$ is identical to $R_5$.

In some embodiments of the present invention, $R_1$, $R_2$, $R_3$, $R_4$, $R_5$, $R_6$, $R_7$ and $R_8$ are each independently selected from hydrogen or deuterium, and $R_9$, $R_{10}$ and $R_{11}$ are each independently selected from hydrogen, provided that at least one of $R_1$, $R_2$, $R_3$, $R_4$, $R_5$, $R_6$, $R_7$ and $R_8$ is selected from deuterium.

In some embodiments of the present invention, $R_1$, $R_2$, $R_3$, $R_4$, $R_5$, $R_6$, $R_7$ and $R_8$ are each independently selected from hydrogen or deuterium, and $R_9$, $R_{10}$ and $R_{11}$ are each independently selected from hydrogen, provided that at least one of $R_1$, $R_2$, $R_3$, $R_4$, $R_5$, $R_6$, $R_7$ and $R_8$ is selected from deuterium, and $R_2$ is identical to $R_3$, $R_4$ is identical to $R_5$, $R_6$ is identical to $R_7$.

In some embodiments of the present invention, $R_1$, $R_2$, $R_3$, $R_4$, $R_5$, $R_6$, $R_7$, $R_8$, $R_9$, $R_{10}$ and $R_{11}$ are each independently selected from hydrogen or deuterium, provided that at least one of $R_1$, $R_2$, $R_3$, $R_4$, $R_5$, $R_6$, $R_7$, $R_8$, $R_9$, $R_{10}$ and $R_{11}$ is selected from deuterium, and when $R_4$ and $R_5$ are selected from deuterium, not all $R_1$, $R_2$, $R_3$, $R_6$, $R_7$, $R_8$, $R_9$, $R_{10}$ and $R_{11}$ are hydrogen.

In some embodiments of the present invention, $R_1$, $R_2$, $R_3$, $R_4$, $R_5$, $R_6$, $R_7$, $R_8$, $R_9$, $R_{10}$ and $R_{11}$ are each independently selected from hydrogen or deuterium, provided that at least one of $R_1$, $R_2$, $R_3$, $R_4$, $R_5$, $R_6$, $R_7$, $R_8$, $R_9$, $R_{10}$ and $R_{11}$ is selected from deuterium, and when $R_4$ and $R_5$ are selected from deuterium, not all $R_1$, $R_2$, $R_3$, $R_6$, $R_7$, $R_8$, $R_9$, $R_{10}$ and $R_{11}$ are hydrogen, and $R_2$ is identical to $R_3$, $R_4$ is identical to $R_5$, $R_6$ is identical to $R_7$.

In some embodiments of the present invention, $R_1$, $R_2$, $R_3$, $R_4$, $R_5$, $R_6$, $R_7$, $R_8$, $R_9$, $R_{10}$ and $R_{11}$ are each independently selected from hydrogen or deuterium, provided that at least one of $R_1$, $R_2$, $R_3$, $R_4$, $R_5$, $R_6$, $R_7$, $R_8$, $R_9$, $R_{10}$ and $R_{11}$ is selected from deuterium, and when $R_1$ and $R_8$ are selected from deuterium, not all $R_1$, $R_2$, $R_3$, $R_4$, $R_5$, $R_6$, $R_7$, $R_8$, $R_9$, $R_{10}$ and $R_{11}$ are hydrogen.

In some embodiments of the present invention, $R_1$, $R_2$, $R_3$, $R_4$, $R_5$, $R_6$, $R_7$, $R_8$, $R_9$, $R_{10}$ and $R_{11}$ are each independently selected from hydrogen or deuterium, provided that at least one of $R_1$, $R_2$, $R_3$, $R_4$, $R_5$, $R_6$, $R_7$, $R_8$, $R_9$, $R_{10}$ and $R_{11}$ is selected from deuterium, and when $R_1$ and $R_8$ are selected from deuterium, not all $R_1$, $R_2$, $R_3$, $R_4$, $R_5$, $R_6$, $R_7$, $R_8$, $R_9$, $R_{10}$ and $R_{11}$ are hydrogen, and $R_2$ is identical to $R_3$, $R_4$ is identical to $R_5$, $R_6$ is identical to $R_7$.

In some embodiments of the present invention, the examples of the compound of Formula I are as follows:

| Number | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| I-1 | H | H | H | H | H | H | H | D | H | H | H |
| I-2 | D | H | H | H | H | H | H | H | H | H | H |
| I-3 | D | H | H | H | H | H | H | D | H | H | H |
| I-4 | H | H | H | D | D | H | H | H | H | H | H |
| I-5 | H | H | H | H | H | D | D | H | H | H | H |
| I-6 | H | D | D | D | D | H | H | H | H | H | H |
| I-7 | D | D | D | H | H | H | H | H | H | H | H |
| I-8 | D | D | D | D | D | H | H | H | H | H | H |
| I-9 | H | D | D | H | H | H | H | H | H | H | H |
| I-10 | H | H | H | H | D | D | D | H | H | H | H |
| I-11 | H | H | H | H | H | H | D | D | D | H | D |
| I-12 | H | H | H | H | H | H | H | D | H | D | D |

In some particular embodiments of the present invention, the compound represented by Formula I is selected from the compounds represented by the following formulas:

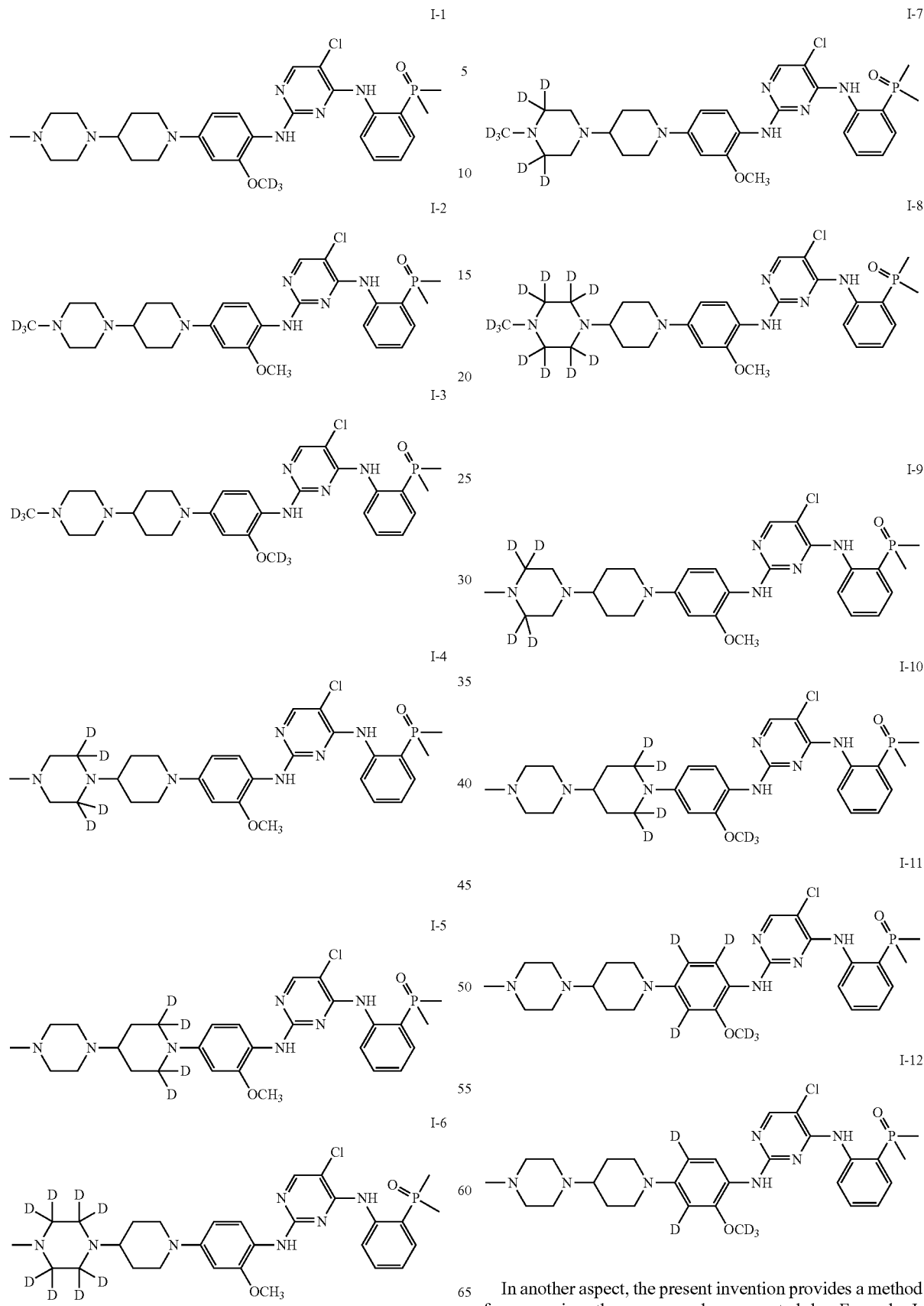
In another aspect, the present invention provides a method for preparing the compound represented by Formula I, including but not limited to the following schemes:

Scheme 1: Synthesis of the compound of Formula I

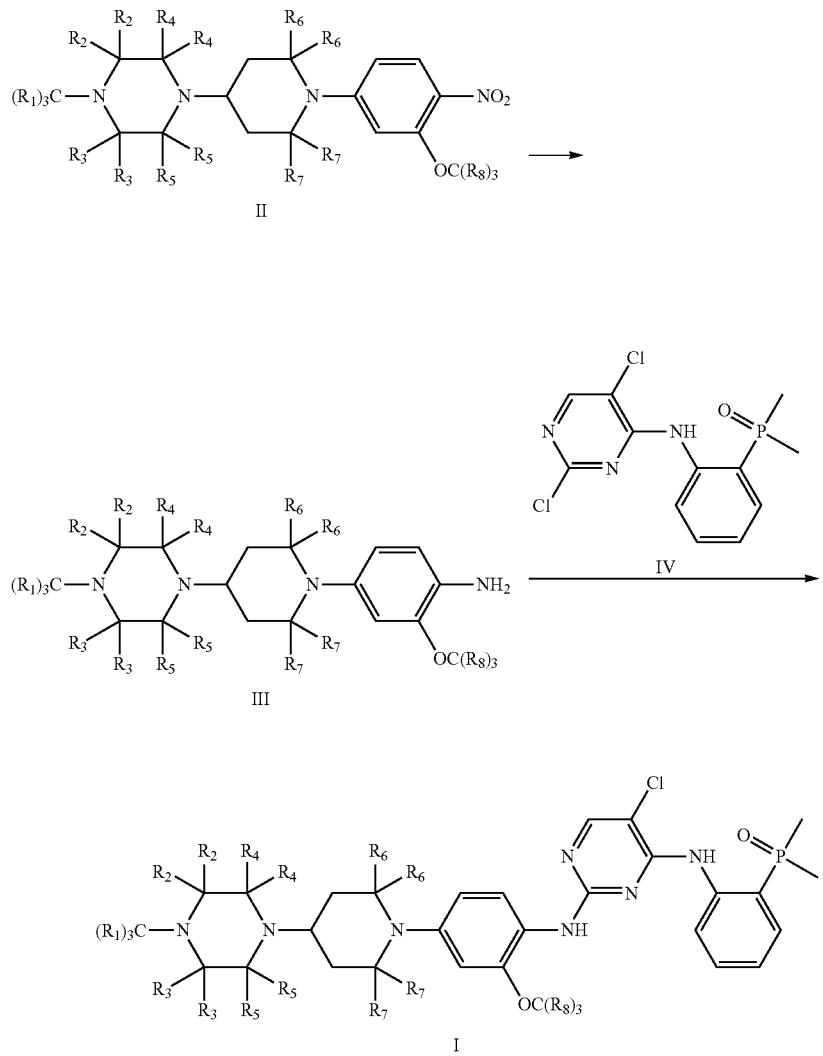

As shown in Scheme 1, a compound of Formula II is reduced by catalytic hydrogenation to give a compound of Formula III; and under the action of an acid, the compound of Formula III is reacted with a compound of Formula IV to give the compound of Formula I.

Scheme 2: Syntheis 1 of a compound of Formula II

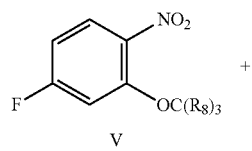

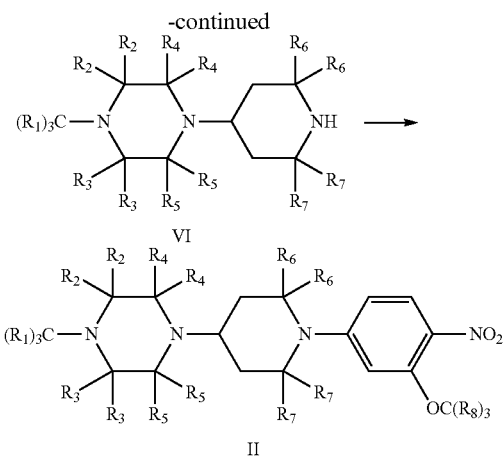

As shown in Scheme 2, compounds of Formulas V and VI take place substitution reaction in the presence of a base to give the compound of Formula II. The compound of Formula VI is commercially available.

Scheme 3: Synthesis 2 of a compound of Formula II

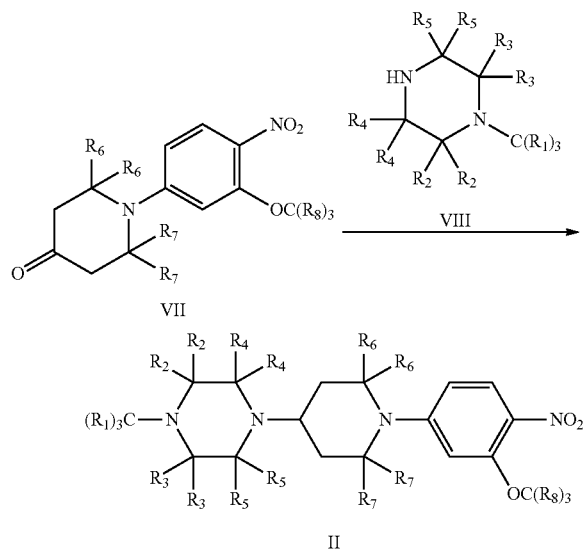

As shown in Scheme 3, compounds of Formulas VII and VIII take place reductive amination reaction, to give the compound of Formula II.

Scheme 4: Synthesis of a compound of Formula VII

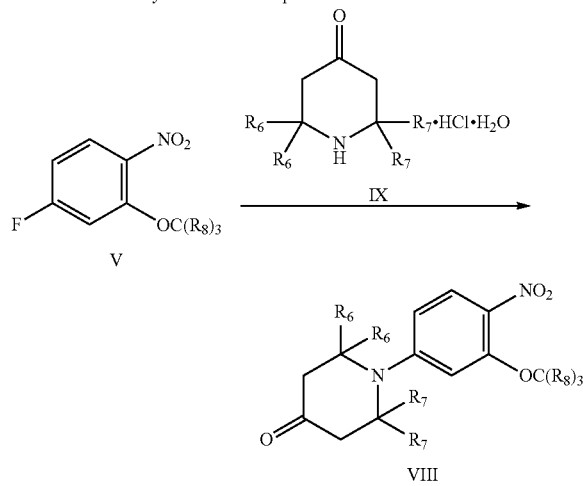

As shown in Scheme 4, a compound of Formula V reacts with a compound of Formula IX in the presence of a base, to give the compound of Formula VII, wherein the compound of Formula IX is commercially available.

Scheme 5: Synthesis of a compound of Formula V

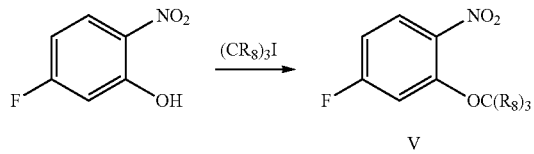

As shown in Scheme 5, 5-fluoro-2-nitrophenol reacts with $C(R_8)_3I$ in the presence of a base, to give the compound of Formula V, wherein 5-fluoro-2-nitrophenol is commercially available.

Scheme 6: Synthesis of a compound of Formula VIII

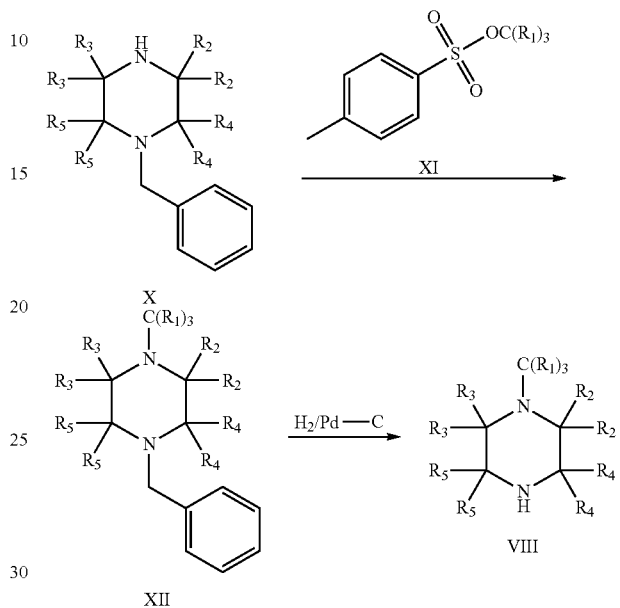

As shown in Scheme 6, a compound of Formula X reacts with a compound of Formula XI to give a compound of Formula XII, and the compound of Formula XII is debenzylated by catalytic hydrogenation of Pd—C to give the compound of Formula VIII. Among them, the compound of Formula X is prepared as the method in CN102675018A, and the compound of Formula XI is commercially available or is prepared as methods known in the art.

Scheme 7: Synthesis of a compound of Formula VIII-2

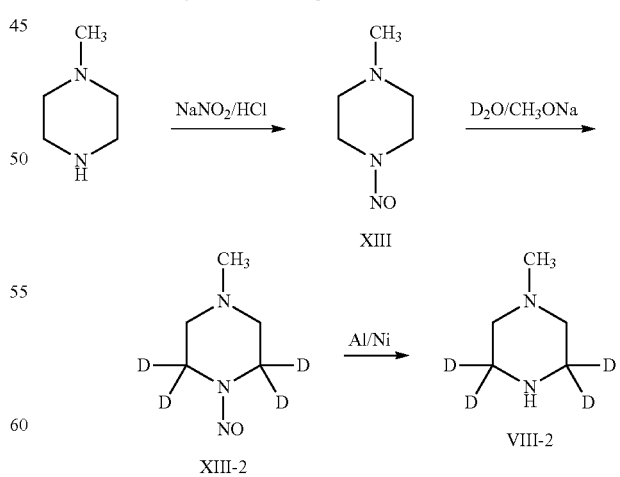

As shown in Scheme 7, 1-methylpiperazine reacts with sodium nitrite in hydrochloric acid to give a compound of Formula XIII, the compound of Formula XIII is treated with heavy water in an alkaline condition to give a deuterated compound of Formula XIII-2, and then the compound of Formula XIII-2 is catalytically reduced to give the compound of Formula VIII-2, wherein 1-methylpiperazine is commercially available.

Scheme 8: Synthesis of a compound of Formula VIII-3

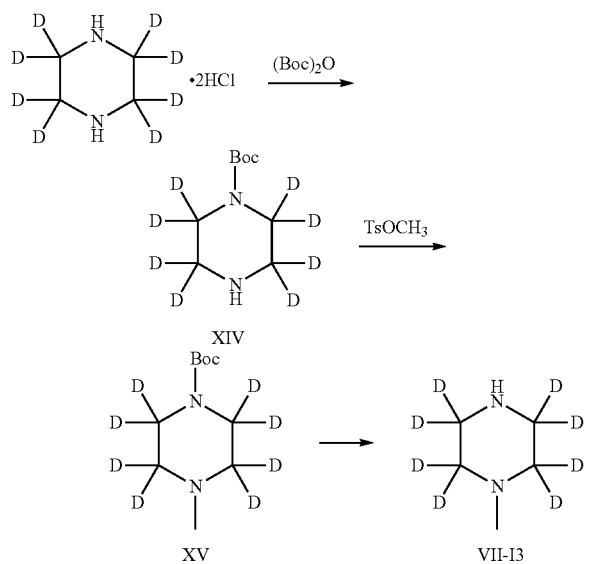

As shown in Scheme 8, deuterated piperazine hydrochloride (which can be prepared as the method in CN201510502945.8) reacts with di-t-butyl dicarbonate in an alkaline condition to give a compound of Formula XIV, the compound of Formula XIV reacts with methyl p-toluenesulfonate under the action of a base to give a compound of Formula XV, the compound of Formula XV is subjected to de-protection under the action of an acid to give an acidic salt of the compound of Formula VIII-3, and then a free compound of Formula VIII-3 is obtained under the action of a base.

Scheme 9: Synthesis of a compound of Formula VIII-4

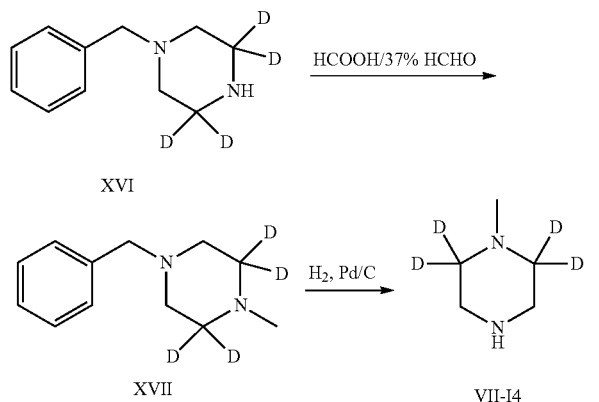

As shown in Scheme 9, a compound of Formula XVI (which can be prepared as the method in CN201510502945.8) undergoes reductive amination reaction in 37% formaldehyde solution and formic acid to give a compound of Formula XVII, and the compound of Formula XVII is debenzylated by catalytic hydrogenation with Pd—C to give the compound of Formula VIII-4.

Scheme 10: Synthesis of the compound of Formula IV

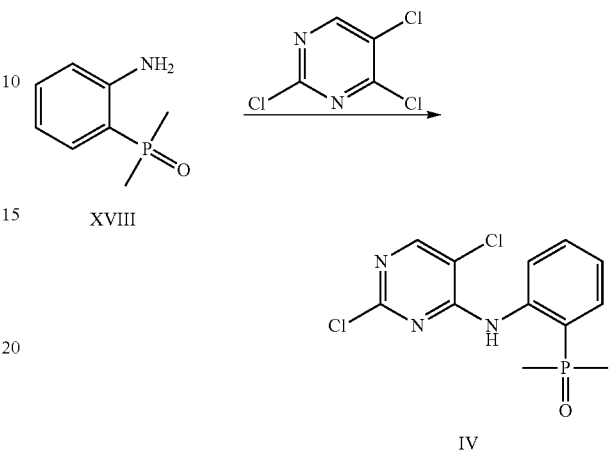

As shown in Scheme 10, the compound of Formula XVIII reacts with 2,4,5-trichloropyrimidine in the presence of alkaline catalysis to give the compound of Formula IV, wherein the compound of Formula XVIII is commercially available.

Among them, deuterated methylating agents (such as deuterated iodomethane) can be commercially available, for example, purchased from Sigma-Aldrich; or can be prepared by known deuteration methods, for example, it can be obtained by exchanging a non-deuterated compound in heavy water in the presence of acid catalyst.

The above Schemes show the synthetic methods constituting the present invention, which are used to describe applicable chemical methods by specific examples, but not present the scope of the present invention or not intended to limit. The chemical structures in the illustrations herein depict variables that are defined, where appropriate, with the definition of the chemical groups at the corresponding positions in the formulas of the compounds herein, whether denoted with the same variable names (i.e., $R_1$, $R_2$, $R_3$ and the like) or not. Appropriateness of a chemical group in a chemical structural formula for synthesizing another compound is within the knowledge of those skilled in the art.

In the description of the preparation method according to the present invention, the definition of the groups $R_1$ to $R_{11}$ in the compounds is described as above.

In another aspect, the present invention provides a pharmaceutical composition, comprising a therapeutically effective amount of a compound of Formula I or a pharmaceutically acceptable salt thereof, and one or more pharmaceutically acceptable carriers or excipients.

The pharmaceutical composition of the present invention can be prepared by combining a compound of the present invention or the pharmaceutically acceptable salt thereof with suitable pharmaceutically acceptable carriers. For example, it can be formulated into solid, semi-solid, liquid or gaseous preparations, such as tablets, pills, capsules, powders, granules, ointments, emulsions, suspensions, solutions, suppositories, injections, inhalants, gels, microspheres, aerosols and the like.

Typical administration routes of compounds of the present invention or pharmaceutically acceptable salts, hydrates, solvates or prodrugs thereof, or pharmaceutical compositions thereof includes, but not limited to, oral, rectal, transmucosal, intestinal administration, or topical, transdermal, inhalation, parenteral, sublingual, intravaginal, intranasal, intraocular, intraperitoneal, intramuscular, subcutaneous, and intravenous administration.

The pharmaceutical composition of the present invention may be manufactured by methods well-known in the art, such as conventional mixing method, dissolution method, granulation method, method for preparing sugar-coated pills, grinding method, emulsification method, freeze-drying method and the like.

For oral administration, the pharmaceutical composition can be formulated by mixing an active compound with a pharmaceutically acceptable carrier well-known in the art. These carriers can allow the compounds of the present invention to be formulated into tablets, pills, troches, dragees, capsules, liquids, gels, slurries, suspensions and the like, for oral administration to patients.

A solid oral composition can be prepared by conventional mixing, filling or tabletingmethod. For example, it can be obtained by the following method: mixing the active compound with solid excipients, optionally milling the resultant mixture, adding additional suitable adjuvants if necessary, and then processing the mixture into granules, to produce tablet cores or dragee cores. Suitable adjuvants include, but not limited to, adhesives, diluents, disintegrants, lubricants, glidants, sweeteners, flavoring agents or the like, such as, microcrystalline cellulose, glucose solution, arabic gum slurry, gelatin solution, sucrose and starch paste; talcum, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, corn starch, potato starch, methylcellulose, agar, carboxymethyl cellulose, crosslinked polyvinylpyrrolidone and the like. The dragee core can be optionally coated, especially with an enteric coating, according to methods recognized in common drug practice.

The pharmaceutical composition can also be suitable for parenteral administration, such as sterile solutions, suspensions or freeze-dried products in a suitable unit dosage form. An appropriate excipient such as a bulking agent, a buffer agent, or surfactant can be used.

The compound represented by Formula I or the pharmaceutically acceptable salt, solvate or prodrug thereof in the present invention can be administered by any suitable routes and methods, for example orally or parenterally (e.g., intravenously). The therapeutically effective amount of the compound of Formula I ranges from about 0.0001 mg/Kg of body weight to 20 mg/Kg of body weight per day, for example from 0.001 mg/Kg of body weight to 10 mg/Kg of body weight per day.

The dose frequency of the compound of Formula I depends on needs of individual patients, for example, once or twice every day or more times every day. Administration can be intermittent, for example, where during a period of several days, patients receives a daily dose of the compound of Formula I, and during a period of next several or more days, they do not receive a daily dose of said compound.

In a further aspect, the present invention provides a method for inhibiting anaplastic lymphoma kinase (AKL), comprising administering a therapeutically effective amount of a compound of Formula I or a pharmaceutically acceptable salt, solvate or prodrug thereof, or a pharmaceutical composition comprising the compound of Formula I, to patients in need thereof.

In further another aspect, the present invention provides a method for treating and/or preventing diseases mediated by anaplastic lymphoma kinase (AKL), comprising administering a therapeutically effective amount of a compound of Formula I or a pharmaceutically acceptable salt, solvate or prodrug thereof, or a pharmaceutical composition comprising the compound of Formula I to patients in need thereof.

In a still further aspect, the present invention provides a use of a compound of Formula I or a pharmaceutically acceptable salt, solvate or prodrug thereof, or a pharmaceutical composition comprising the compound of Formula I in the manufacture of a medicament for treating and/or preventing diseases mediated by anaplastic lymphoma kinase (AKL).

A further aspect of the present invention is to provide a pharmaceutical composition comprising a compound represented by Formula I or a pharmaceutically acceptable salt thereof, for treating and/or preventing diseases mediated by anaplastic lymphoma kinase (AKL).

In some embodiments of the present invention, diseases mediated by anaplastic lymphoma kinase (AKL) are cancer. The cancer is selected from ovarian cancer, cervical cancer, colorectal cancer, breast cancer, pancreatic cancer, glioma, glioblastoma, melanoma, prostate cancer, leukemia, lymphoma, Non-Hodgkin's lymphoma, stomach cancer, lung cancer, hepatocellular carcinoma, gastrointestinal stromal tumor, thyroid cancer, biliary duct cancer, endometrial cancer, renal cancer, anaplasia large cell lymphoma, acute myeloid leukemia, multiple myeloma, melanoma and mesothelioma. The lung cancer is selected from non-small cell lung cancer, small cell lung cancer, lung adenocarcinoma, and lung squamous cell carcinoma.

The compound of Formula I or the pharmaceutically acceptable salt, solvate or prodrug thereof, or the pharmaceutical composition comprising the compound of Formula I according to the present invention can be also for use in the manufacture of a medicament for treating and/or preventing cardiovascular diseases, inflammation, infection, immune diseases, cell proliferative diseases, viral diseases, metabolic diseases and organ transplantation.

Related Definition

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to a salt that retains the biological effectiveness of the free acids and free bases of a specific compound, which are not biologically or otherwise undesirable. Examples of the pharmaceutically acceptable salt include, but not limited to, (1) acid addition salts such as, salts formed with inorganic acids such as hydrochloric acid, sulfuric acid, hydrobromic acid, nitric acid, phosphoric acid and the like, or salts formed with organic acids such as malic acid, fumaric acid, maleic acid, benzoic acid, phenylacetic acid, succinic acid, tartaric acid, citric acid, methanesulfonic acid, ethanesulfonic acid, glycolic acid, cinnamic acid, pyruvate, formic acid, acetic acid, propionic acid, oxalic acid, malonic acid, acrylic acid, mandelic acid and the like; or (2) base addition salts such as, salts formed with alkali metals such as lithium, sodium, potassium and the like, salts formed with alkaline earth metal such as calcium, magnesium and the like, and salts formed with organic bases such as ammonium, choline, diethanolamine, lysine, ethylenediamine, t-butylamine, t-octylamine, tris(hydroxymethyl)aminomethane, N-methyl glucosamine, triethanolamine, dehydroabietylamine and the like.

The pharmaceutically acceptable salt of the present invention can be synthesized from a parent compound containing an acid or alkali group by conventional chemical methods. In general, such a salt is prepared by a method of allowing these compounds in the form of free acid or base to react with a stoichiometric amount of an appropriate base or acid in water or an organic solvent, or a mixture thereof.

The term "solvate" or "solvates" includes hydrates and solvent addition forms and salts thereof, which are able to be formed by the compound of Formula I. Examples of such forms are hydrates, alcoholates or the like.

If not specified, any atom of the compounds labeling-synthesized in the present invention will represent any one of stable isotopes of this atom. When a position in the structure is defined as H, i.e., hydrogen (H-1), unless otherwise specifically stated, this position only contains naturally occurring isotopes. Likewise, when a position in the structure is defined as D, i.e., deuterium (H-2), unless otherwise specifically stated, the amount of the isotope at this position is at least 3340 times greater than that of naturally occurring isotopes (0.015%) (i.e., at least 50.1% isotope deuterium is contained). When one or several positions in the structure of a compound labeling-synthesized are defined as D, i.e., deuterium (H-2), the compound represented by the structure can be at least 52.5%, at least 60%, at least 67.5%, at least 75%, at least 82.5%, at least 90%, at least 95%, at least 97%, at least 98.5%, at least 99%, and at least 99.5%. A deuterated ratio of the compound labeling-synthesized in the present invention refers to a ratio value of the content of a labeled synthetic isotope to the content of naturally occurring isotopes. The deuterated ratio of each indicated atom in the compound labeling-synthesized according to the present invention can be at least 3500 fold (52.5%), at least 4000 fold (60%), at least 4500 fold (67.5%), at least 5000 fold (75%), at least 5500 fold (82.5%), at least 6000 fold (90%), at least 6333.3 fold (95%), at least 6466.7 fold (97%), at least 6566.7 fold (98.5%), at least 6600 fold (99%), at least 6633.3 fold (99.5%). Isotopologues in the present invention refers to compounds that differ merely by different isotopic composition in terms of chemical structure. The compounds labeling-synthesized in the present invention have the same chemical structure and only have differences in isotope in atomic composition of their molecules. Therefore, the compound having deuterium at a specific position labeling-synthesized in the present invention also contains very few hydrogen isotopologue at this position. The amount of hydrogen isotopologue at a position in the compound labeling-synthesized in the present invention depends on many factors, including isotope deuterium purity of deuterated reagents ($D_2O$, $D_2$, $NaBD_4$, $LiAlD_4$, etc.) and effectiveness of the synthesis methods for introducing isotope deuterium. However, as mentioned above, the total amount of hydrogen isotopologue at such a position will be less than 49.9%. The total amount of hydrogen isotopologue at a position in a compound labeling-synthesized in the present invention will be less than 47.5%, 40%, 32.5%, 25%, 17.5%, 10%, 5%, 3%, 1% or 0.5%.

In the present invention, any atom that is not specified as deuterium exists at natural isotope abundance thereof.

The term "pharmaceutically acceptable carrier" refers to a carrier that does not cause significant irritation to an organism and does not abrogate the biological activity and properties of the active compound. The "pharmaceutically acceptable carrier" refers to an inert material that is administered together with an active ingredient and facilitates the administration of the active ingredient, including but not limited to, any glidants, sweeteners, diluents, preservatives, dyes/coloring agents, flavor enhancers, surfactants, wetting agents, dispersants, disintegrants, suspending agents, stabilizers, isotonic agents, solvent or emulsifier. Non-limited examples of the carriers include calcium carbonate, calcium phosphate, various carbohydrates and various kinds of starch, cellulose derivatives, gelatin, vegetable oils, polyethylene glycol and the like. Other information about the carriers can refer to Remington: The Science and Practice of Pharmacy, 21st Ed., Lippincott, Williams & Wilkins (2005), the contents of which is incorporated herein by reference.

The term "excipient" or "excipients" usually refers to a carrier, diluent and/or medium required for formulating an effective pharmaceutical composition.

For a drug or pharmaceutical active agent, the term "effective amount" or "therapeutically effective amount" means a nontoxic but sufficient amount of the drug or agent to provide the desired effect. In the oral dosage forms of the present invention, an "effective amount" of one active substance in the composition refers to the amount of that substance that is required to provide the desired effect when used in combination with the other active substance of the composition. The determination of an effective amount varies from person to person, depending upon the age and general conditions of the subject, and also depending upon the specific active substance. A suitable effective amount in each individual case can be determined by those skilled in the art according to routine testing.

Unless otherwise indicated, all raw materials are commercial and will not be further purified prior to being used. Silica gel (200-300 mesh) produced by Qingdao Haiyang Chemical Co., Ltd is employed in the column chromatography used in the present invention. Thin layer chromatography is produced by Qingdao MaKall Group Inc. Instruments used for NMR spectroscopy are BRUKER-300 and BRUKER-500 resonance spectrometers, tetramethylsilane (TMS=δ 0.00) as an internal standard for a chemical shift, and the data of NMR spectroscopy is recorded in a format of: proton number, peak shapes (s, singlet; d, doublet; t, triplet; q, quartet; m, multiplet), coupling constant (in Hertz, Hz). AB SCIEX Triple TOF 4600 is used for mass spectrometry.

The following abbreviations are used in the present invention: Boc- represents t-butyloxycarbonyl; DMF represents N,N-dimethylformamide.

The compounds represented by Formula I of the present invention (for example, in the situations that $R_1$ is deuterium, $R_2$ and $R_3$ are deuterium, $R_4$ and $R_5$ are deuterium or $R_8$ is deuterium, particularly in the situations that $R_1$ is deuterium, $R_2$ and $R_3$ are deuterium or $R_8$ is deuterium, especially in the situations of the compounds in Examples) have better pharmacokinetic properties as compared to Brigatinib and have an excellent inhibitory activity against anaplastic lymphoma kinase (ALK).

SPECIFIC EMBODIMENTS The present invention will be described by the following examples in more details, which do not limit the present invention by any means.

It should be noted that in the following examples, the preparation methods of the compounds are described by taking only I-1 (Example 1), I-2 (Example 3), I-3 (Example 5), I-4 (Example 6), I-6 (Example 7), I-7 (Example 8) and I-9 (Example 9) as examples. However, since the present invention focuses on the deuterium-modified Brigatinib derivatives, the methods for preparing the compounds according to the present invention are similar. Therefore, the compounds within the scope of the claims of the present invention can be prepared by using methods similar to those described in the Description of the present invention and the following examples.

EXAMPLE 1

Preparation of 2-((5-chloro-2-((2-[D₃]methoxy-4-(4-(4-methylpiperazin-1-yl)piperidin-1-yl)phenyl)amino)pyrimidin-4-yl)amino)phenyl)dimethyl phosphorus oxide (the compound of Formula I-1)

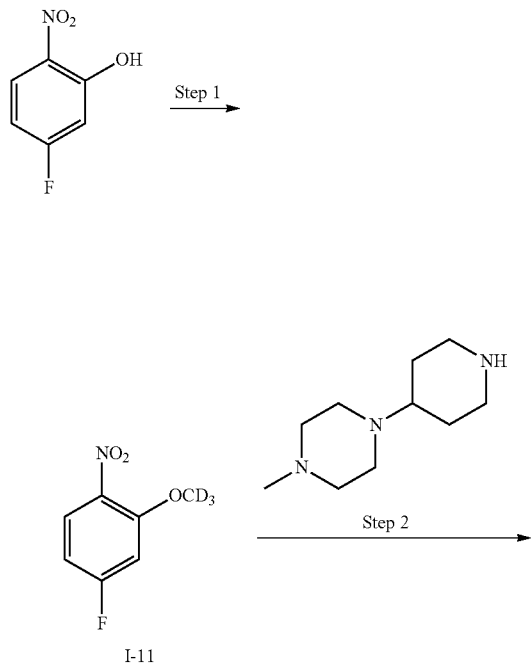

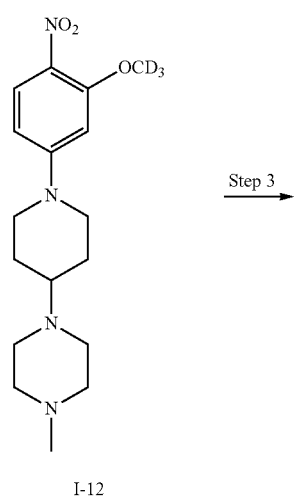

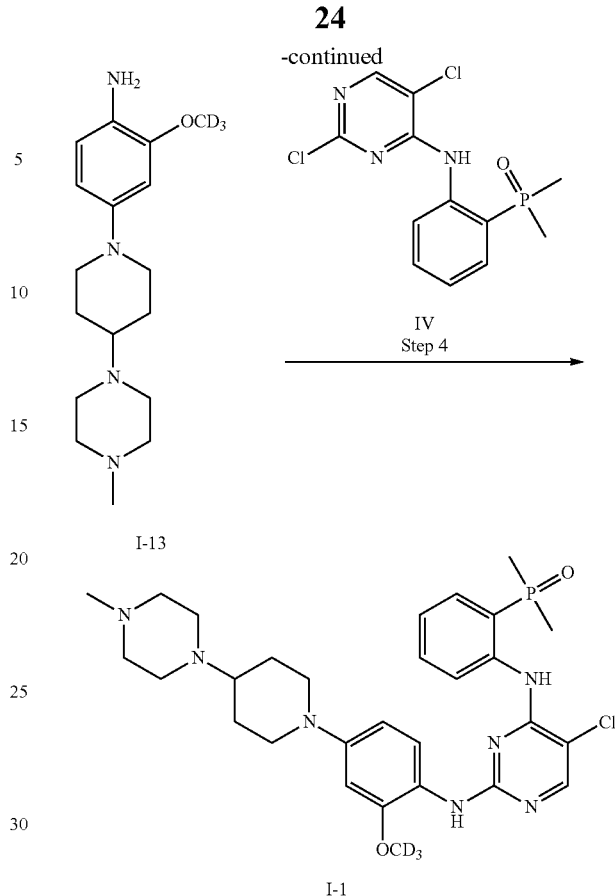

Step 1: Preparation of 4-fluoro-2-[D₃]methoxy-1-nitrobenzene (the compound of Formula I-11)

5-fluoro-2-nitrophenol (15.7 g, 100 mmol), anhydrous potassium carbonate (13.8 g, 100 mmol) and acetone (150 mL) were respectively added in a 250 mL three-necked flask and stirred at room temperature for 100 minutes, and then deuterated iodomethane (6.2 mL, 100 mmol) was slowly added dropwise. After the dropwise addition, the mixture was heated to reflux and react for 9 hours. After the reaction was completed, the reaction solution was cooled down to room temperature and filtered by suction. The filtrate was evaporated under reduced pressure to remove the solvent, added with 10% sodium hydroxide aqueous solution (100 mL), stirred vigorously, extracted with ethyl acetate (100 mL×3), dried over anhydrous sodium sulfate and evaporated under reduced pressure to remove the solvent, to give 4-fluoro-2-[D₃]methoxy-1-nitrobenzene (17.7 g) with >98% of D₃ content.

$^1$H-NMR (300 MHz, CDCl₃): δ=7.97-7.92 (dd, J=6.0, 8.9 Hz, 1H), 6.81-6.69 (m, 2H).

Step 2: Preparation of 1-(1-(3-[D₃]methoxy-4-nitrophenyl)piperidin-4-yl)-4-methylpiperazine (the compound of Formula I-12)

A mixture of 4-fluoro-2-[D₃]methoxy-1-nitrobenzene (2.12 g, 12.17 mmol), 1-methyl-4-(4-piperidinyl)piperazine (2.23 g, 12.17 mmol) and anhydrous potassium carbonate (3.37 g, 24.34 mmol) in DMF (20 mL) was heated to 120° C. and reacted for 6 hours. After the reaction was completed, the reaction solution was cooled, filtered by suction, and evaporated under reduced pressure to remove the solvent, followed by adding dichloromethane (60 mL) and water (30 mL), and stirring to separate layers. The aqueous layer was extracted with dichloromethane (30 mL×6). The organic phase was combined, washed with saturated brine (60 mL), dried over anhydrous sodium sulfate, filtered by suction and evaporated under reduced pressure to remove the solvent, to give 1-(1-(3-[D$_3$]methoxy-4-nitrophenyl)piperidin-4-yl)-4-methylpiperazine (2.95 g, 72.0% yield), with >98% of D$_3$ content.

$^1$H-NMR (300 MHz, CDCl$_3$): δ=7.98 (d, J=9.3 Hz, 1H), 6.41 (dd, J=2.4, 9.3 Hz, 1H), 6.30 (d, J=2.0 Hz, 1H), 3.94 (d, J=13.2 Hz, 2H), 2.96 (t, J=12.0 Hz, 2H), 2.62-2.45 (m, 9H), 2.29 (s, 3H), 1.96 (d, J=12.5 Hz, 2H), 1.63-1.54 (m, 2H).

HRMS (ESI, [M+H]$^+$) m/z: 338.2254.

Step 3: Preparation of 2-[D$_3$]methoxy-4-(4-(4-methylpiperazin-1-yl)piperidin-1-yl)aniline (the compound of Formula I-13)

1-(1-(3-[D$_3$]methoxy-4-nitrophenyl)piperidin-4-yl)-4-methylpiperazine (0.59 g, 1.7 mmol) was dissolved in anhydrous methanol (30 mL) and added with 10% Pd—C (0.12 g), and hydrogenation reaction was allowed to proceed overnight at room temperature. After the reaction was completed, the reaction solution was filtered by suction and evaporated under reduced pressure to remove the solvent, to give 2-[D$_3$]methoxy-4-(4-(4-methylpiperazin-1-yl)piperidin-1-yl)aniline (0.45 g, 86.5% yield), with >98% of D$_3$ content.

$^1$H-NMR (300 MHz, CDCl$_3$): δ=6.62 (d, J=8.3 Hz, 1H), 6.51 (d, J=2.4 Hz, 1H), 6.41 (dd, J=2.4, 8.4 Hz, 1H), 3.53-3.49 (m, 3H), 2.83-2.33 (m, 10H), 2.29 (s, 3H), 1.92 (d, J=12.2 Hz, 2H), 1.77-1.64 (m, 2H).

HRMS (ESI, [M+H]$^+$) m/z: 308.2525.

Step 4: Preparation of (2-((5-chloro-2-((2-[D$_3$]methoxy-4-(4-(4-methylpiperazin-1-yl)piperidin-1-yl)phenyl)amino)pyrimidin-4-yl)amino)phenyl)dimethyl phosphorus oxide (the compound of Formula I-1)

2-[D$_3$]methoxy-4-(4-(4-methylpiperazin-1-yl)piperidin-1-yl)aniline (1.25 g, 4.06 mmol), (2-((2,5-dichloropyrimidin-4-yl)amino)phenyl)dimethyl phosphine oxide (the compound of Formula IV) (0.92 g, 2.90 mmol), 14% hydrogen chloride-ethanol (7.5 g, 29 mmol) and ethylene glycol monomethyl ether (22 mL) were respectively added in a 35 mL pressure tubing, heated in a microwave to 120° C. and reacted for 5.5 hours. After the reaction was completed, the reaction solution was cooled down to room temperature and evaporated under reduced pressure to remove the solvent. The residue was dissolved in dichloromethane (60 mL) and adjusted to alkaline pH by adding saturated sodium carbonate solution. The resulting solution was separated. The organic phase was washed with saturated brine (30 mL), dried over anhydrous sodium sulfate, and evaporated under reduced pressure to remove the solvent. The residue obtained was subjected to silica gel column chromatography (mobile phase, dichloromethane:methanol:triethylamine=300:30:1.5) to give a crude product. The crude product was beaten with ethyl acetate (10 mL) to give (2-((5-chloro-2-((2-[D$_3$]methoxy-4-(4-(4-methylpiperazin-1-yl)piperidin-1-yl)phenyl)amino)pyrimidin-4-yl)amino)phenyl)dimethyl phosphorus oxide (0.18 g, 11.0% yield), with >98% of D$_3$ content.

$^1$H-NMR (300 MHz, CDCl$_3$): δ=10.80 (s, 1H), 8.62 (dd, J=4.4, 8.2 Hz, 1H), 8.09-8.08 (m, 2H), 7.47 (dd, J=7.7, 8.0 Hz, 1H), 7.31-7.25 (m, 1H), 7.11 (dd, J=7.4, 7.0 Hz, 1H), 6.54 (s, 1H), 6.48 (dd, J=1.4, 8.4 Hz, 1H), 3.65 (d, J=12.2 Hz, 2H), 2.73-2.41 (m, 11H), 2.37 (s, 3H), 1.95 (d, J=11.2 Hz, 2H), 1.85, 1.80 (2s, 6H), 1.73-1.66 (m, 2H).

$^{13}$C-NMR (75 MHz, CDCl$_3$): δ=157.76, 155.87, 154.93, 149.29, 147.48, 143.90, 143.87, 132.33, 132.30, 129.52, 129.37, 123.10, 123.01, 122.44, 122.27, 122.09, 120.58, 119.55, 108.36, 105.99, 101.01, 61.78, 55.27, 50.46, 48.78, 45.83, 28.19, 19.02, 18.08.

HRMS (ESI, [M+H]$^+$) m/z: 587.2861.

EXAMPLE 2

Preparation of (2-((2,5-Dichloropyrimidin-4-Yl)Amino)Phenyl)Dimethyl Phosphorus Oxide (the Compound of Formula IV)

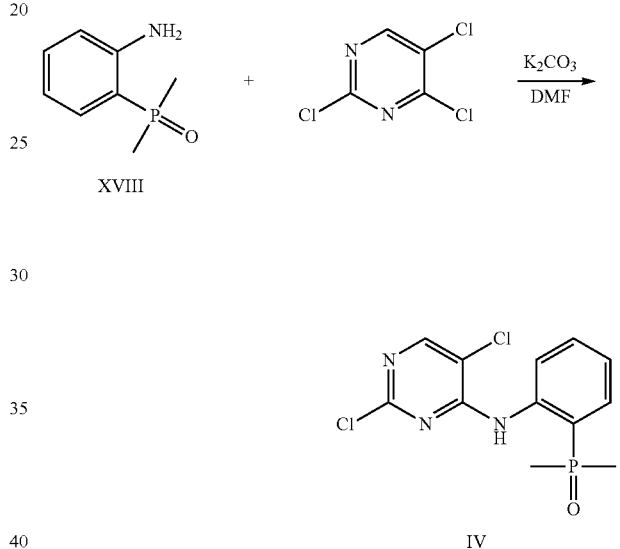

(2-aminophenyl)dimethyl phosphorus oxide (8.76 g, 51.81 mmol), 2,4,5-trichloropyrimidine (14.92 g, 81.35 mmol), anhydrous potassium carbonate (22.49 g, 162.29 mmol) and N,N-dimethylformamide (50 mL) were added in a 100 mL single-necked flask, and the mixture was heated to 60° C. and reacted for 5 hours. After the reaction was completed, the reaction solution was cooled down to room temperature, added with water (30 mL) and extracted with dichloromethane (100 mL×3), washed with saturated brine (100 mL), dried over anhydrous sodium sulfate, filtered by suction, and evaporated under reduced pressure to remove the solvent. The resulting crude product was subjected to silica gel column chromatography (mobile phase, dichloromethane:methanol=40:1) to give (2-((2,5-dichloropyrimidin-4-yl)amino)phenyl)dimethyl phosphorus oxide (11.3 g, 69.0% yield).

$^1$H-NMR (300 MHz, CDCl$_3$): δ=11.55 (s, 2H), 8.67 (dd, J=4.4, 8.5 Hz, 1H), 8.22 (s, 1H), 7.59 (dd, J=7.7, 8.1 Hz, 1H), 1.86 (s, 3H), 1.82 (s, 3H).

$^{13}$C-NMR (75 MHz, CDCl$_3$): δ=156.85, 155.10, 133.05, 133.03, 129.77, 129.63, 123.56, 123.40, 122.18, 122.09, 19.28, 18.33.

HRMS (ESI, [M+H]$^+$) m/z: 316.0175.

EXAMPLE 3

Preparation of (2-((5-chloro-2-((2-methoxy-4-(4-(4-[D$_3$]methylpiperazin-1-yl)piperidin-1-yl)phenyl)amino)pyrimidin-4-yl)amino)phenyl)dimethyl phosphorus oxide (the compound of Formula I-2)

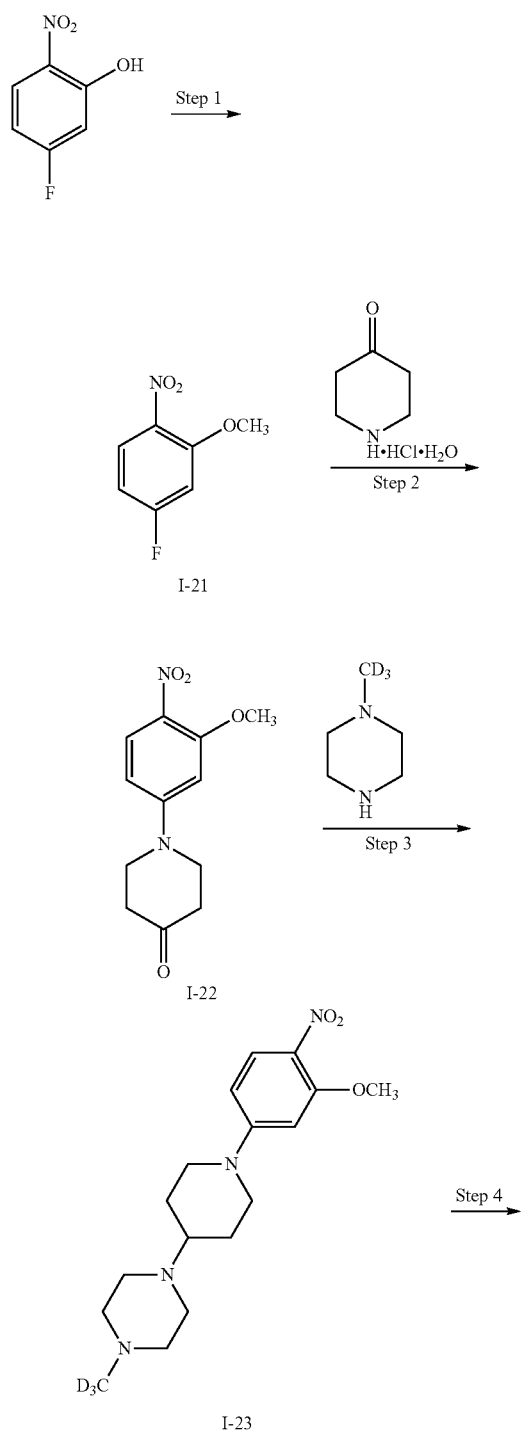

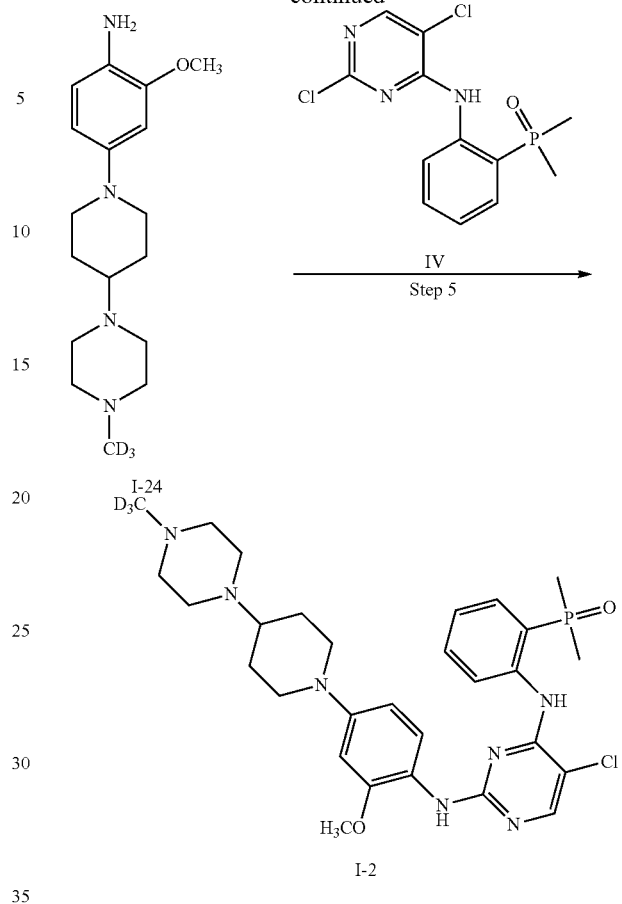

Step 1: Preparation of 4-fluoro-2-methoxynitrobenzene (the compound of Formula I-21)

5-fluoro-2-nitrophenol (10 g, 63.65 mmol), potassium carbonate (8.8 g, 63.65 mmol) and acetone (100 mL) were added in a 250 mL three-necked flask and stirred at room temperature for 30 minutes under the protection of nitrogen gas. Iodomethane (9.03 g, 63.65 mmol) was then slowly added dropwise thereto, and the mixture was warmed up to 60° C. and reacted overnight. After the reaction was completed, the reaction solution was added with water (200 mL), extracted with ethyl acetate (100 mL×4), washed with 1M sodium hydroxide (100 mL×3) and saturated brine (100 mL×2) successively, dried over anhydrous sodium sulfate, filtered by suction and evaporated under reduced pressure to remove the solvent, to give 4-fluoro-2-methoxynitrobenzene (10.8 g, 99.1% yield).

Step 2: Preparation of 1-(3-methoxy-4-nitrophenyl)piperidin-4-one (the compound of Formula I-22)

4-fluoro-2-methoxynitrobenzene (3.4 g, 20 mmol), piperidone hydrochloride monohydrate (3.4 g, 22 mmol), anhydrous potassium carbonate (6.9 g, 50 mmol) and DMF (400 mL) were respectively added in a 100 mL single-necked flask, and the mixture was heated to 75° C. and reacted for 18 hours. After the reaction was completed, the reaction solution was cooled down to room temperature, filtered by suction and evaporated under reduced pressure to remove the solvent. The residue was dissolved in dichloromethane (600 mL), washed with water (60 mL) and saturated brine (60 mL) respectively, dried anhydrous sodium sulfate, filtered by suction and evaporated under reduced pressure to remove the solvent, to give a crude product. The crude product was beaten with n-hexane (200 mL) and filtered by suction to give 1-(3-methoxy-4-nitrophenyl)piperidin-4-one (2.12 g, 42.4% yield).

$^1$H-NMR (300 MHz, CDCl$_3$): δ=8.04 (d, J=9.2 Hz, 1H), 6.46 (dd, J=9.2, 2.3 Hz, 1H), 6.38 (d, J=2.2 Hz, 1H), 3.97 (s, 3H), 3.79 (t, J=6.0 Hz, 4H), 2.65 (t, J=6.0 Hz, 4H).

Step 3: Preparation of 1-(1-(3-methoxy-4-nitrophenyl)piperidin-4-yl)-4-[D$_3$]methylpiperazine (the compound of Formula I-23)

1-(3-methoxy-4-nitrophenyl)piperidin-4-one (2.20 g, 8.8 mmol) was dissolved in 1,2-dichloroethane (30 mL), and then anhydrous magnesium sulfate (6.0 g), acetic acid (0.53 mL, 8.8 mmol) and 1-[D$_3$]methylpiperazine (1.80 g, 17.6 mmol) were respectively added thereto, followed by stirring at room temperature for 1 hour. Sodium triacetoxyborohydride (2.24 g, 1.2 mmol) was added portionwise in an ice bath, and the mixture was heated to room temperature and reacted for 5 hours after addition. After the reaction was completed, the reaction solution was added with solid sodium carbonate (6 g), stirred for 30 minutes and filtered by suction. The filter cake was washed with dichloromethane (2×30 mL), further washed with saturated sodium carbonate aqueous solution (30 mL) and saturated brine (60 mL) respectively, dried over anhydrous sodium sulfate, filtered by suction and evaporated under reduced pressure to remove the solvent, to give a crude product. The crude product was subjected to silica gel column chromatography (mobile phase, dichloromethane:methanol=20:1 to 6:1) to give 1-(1-(3-methoxy-4-nitrophenyl)piperidin-4-yl)-4-[D$_3$]methylpiperazine (1.17 g, 39.4% yield), with >98% of D$_3$ content.

$^1$H-NMR (300 MHz, CDCl$_3$): δ=7.99 (d, J=9.5 Hz, 1H), 6.41 (dd, J=2.5, 9.5 Hz, 1H), 6.31 (d, J=2.5 Hz, 1H), 3.96-3.93 (m, 5H), 2.96 (td, J=2.5, 12.5 Hz, 2H), 2.63-2.4 (m, 9H), 1.98 (d, J=12.5 Hz, 2H), 1.63 (qd, J=3.5, 12.5 Hz, 2H).

HRMS (ESI, [M+H]$^+$) m/z: 338.2201.

Step 4: Preparation of 2-methoxy-4-(4-(4-[D3]methylpiperazin-1-yl)piperidin-1-yl)aniline (the compound of Formula I-24)

1-(1-(3-methoxy-4-nitrophenyl)piperidin-4-yl)-4-[D$_3$]methylpiperazine (1.12 g, 3.3 mmol) was dissolved in anhydrous methanol (25 mL) and added with 10% Pd—C (0.11 g), and hydrogenation reaction was allowed to proceed overnight at room temperature. After the reaction was completed, the reaction solution was filtered by suction and evaporated under reduced pressure to remove the solvent, to give 2-methoxy-4-(4-(4-[D$_3$]methylpiperazin-1-yl)piperidin-1-yl)aniline (0.97 g, 96.0% yield), with >98% of D$_3$ content.

$^1$H-NMR (300 MHz, CDCl$_3$): δ=6.65 (d, J=8.0 Hz, 1H), 6.54 (d, J=2.5 Hz, 1H), 6.43 (dd, J=2.0, 8.5 Hz, 1H), 3.85 (s, 3H), 3.53 (d, J=12.5 Hz, 2H), 2.65-2.34 (m, 11H), 1.94 (d, J=12 Hz, 2H), 1.73 (qd, J=3.5, 12.5 Hz, 2H).

HRMS (ESI, [M+H]$^+$) m/z: 308.2466.

Step 5: Preparation of (2-((5-chloro-2-((2-methoxy-4-(4-(4-[D$_3$]methylpiperazin-1-yl)piperidin-1-yl)phenyl) amino)pyrimidin-4-yl)amino)phenyl)dimethyl phosphorus oxide (the compound of Formula I-2)

As Step 4 in Example 1, (2-((5-chloro-2-((2-methoxy-4-(4-(4-[D$_3$]methylpiperazin-1-yl)piperidin-1-yl)phenyl) amino)pyrimidin-4-yl)amino)phenyl)dimethyl phosphorus oxide (0.45 g, 32.4% yield) with >98% of D$_3$ content was obtained.

$^1$H-NMR (300 MHz, CDCl$_3$): δ=10.80 (s, 1H), 8.62 (dd, J=4.3, 8.3 Hz, 1H), 8.09-8.08 (m, 2H), 7.47 (dd, J=7.6, 7.7 Hz, 1H), 7.31-7.27 (m, 1H), 7.11 (dd, J=6.5, 7.2 Hz, 1H), 6.55 (s, 1H), 6.48 (d, J=8.7 Hz, 1H), 3.86 (s, 3H), 3.65 (d, J=11.7 Hz, 2H), 2.70-2.41 (m, 11H), 1.96 (d, J=11.5 Hz, 2H), 1.86,1.80 (2s, 6H), 1.74-1.66 (m, 2H).

$^{13}$C-NMR (75 MHz, CDCl$_3$): δ=157.75, 155.85, 154.89, 149.31, 147.46, 143.87, 143.84, 132.28, 129.49, 129.34, 123.08, 122.98, 122.41, 122.25, 122.06, 120.82, 120.60, 119.55, 108.36, 105.96, 101.00, 61.75, 55.28, 55.13, 50.40, 48.71, 28.16, 18.99, 18.04.

HRMS (ESI, [M+H]$^+$) m/z: 587.2780.

EXAMPLE 4

Preparation of 1-[D$_3$]Methylpiperazine

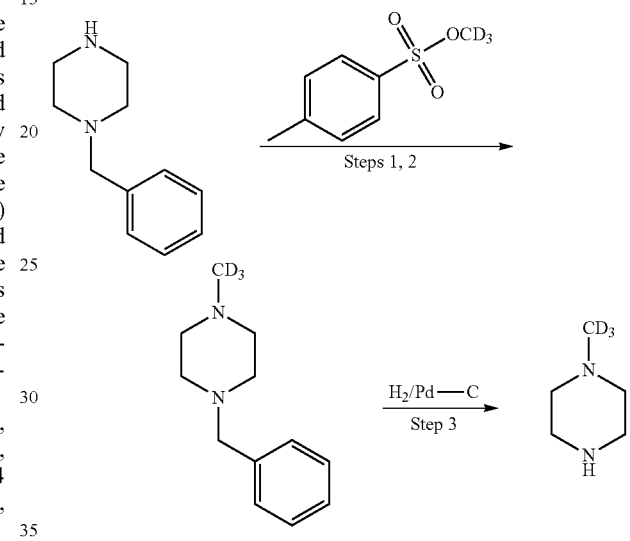

Step 1: Preparation of 4-methylbenzenesulfonic acid [D$_3$] methyl ester

Granulated sodium hydroxide (27.7 g, 693.7 mmol) and water (50 mL) were added in a 500 mL three-necked flask and dissolve after stirring, and the solution was cooled down to 0° C. A solution of p-toluenesulfonyl chloride (31.74 g, 166.48 mmol) in anhydrous tetrahydrofuran (50 mL) was then slowly added dropwise thereto at 0° C., and the resulting solution was warmed up to room temperature and stirred overnight after dropwise addition. After the reaction was completed, the reaction solution was neutralized by slowly adding dropwise with acetic acid (31.7 g) at 20° C., extracted with ethyl acetate (3×100 mL), washed with saturated sodium carbonate aqueous solution (100 mL) and saturated brine (100 mL) respectively, dried over anhydrous sodium sulfate and evaporated under reduced pressure to remove the solvent, to give 4-methylbenzenesulfonic acid [D$_3$]methyl ester (20.62 g, 78.5% yield), with >98% of D$_3$ content.

$^1$H-NMR (300 MHz, CDCl$_3$): δ=7.78 (d, J=8.0 Hz, 2H), 7.36 (d, J=7.9 Hz, 2H), 2.45 (s, 3H).

Step 2: Preparation of 1-benzyl-4-[D$_3$]methylpiperazine 1-benzylpiperazine (17.63 g, 100 mmol) and dried tetrahydrofuran (70 mL) were added in a 250 mL single-necked flask, cooled down to 0° C., added portionwise with 60% sodium hydride (4.0 g, 100 mmol) and stirred at room temperature for 30 minutes. After cooling down to 0° C., a solution of 4-methylbenzenesulfonic acid [D$_3$]methyl ester (9.46 g, 50 mmol) in tetrahydrofuran (10 mL) was slowly added dropwise thereto, followed by naturally warming up to room temperature and stirred overnight. After the reaction was completed, the reaction solution was filtered by suction. The filter cake was washed with ethyl acetate (3×20 mL), and evaporated under reduced pressure to remove the solvent, to give a crude product. 1-benzyl-4-[D$_3$]methylpiperazine (5.2 g, 54.7% yield) with >98% of D$_3$ content was then obtained by column chromatography.

$^1$H-NMR (300 MHz, CDCl$_3$): δ=7.31-7.23 (m, 5H), 3.5 (s, 2H), 2.72-2.26 (m, 8H).

HRMS (ESI, [M+H]$^+$) m/z 194.1683.

Step 3: Preparation of 1-[D$_3$]methylpiperazine 1-benzyl-4-[D$_3$]methylpiperazine (5.2 g, 26.77 mmol) was dissolved in anhydrous methanol (30 mL) and added with 10% Pd—C (0.8 g), and hydrogenation reaction was allowed to proceed at 40° C. for 12 hours. After cooling down to room temperature, the reaction solution was filtered by suction and re-added with 10% Pd—C (0.8 g), and additional hydrogenation reaction were performed at 40° C. for 12 hours. After cooling, the reactant was filtered by suction and evaporated under reduced pressure at 40° C. to remove the solvent, to give 1-[D$_3$]methylpiperazine (3.38 g, 100% yield), with >98% of D$_3$ content.

HRMS (ESI, [M+H]$^+$) m/z:104.1247.

EXAMPLE 5

Preparation of (2-((5-chloro-2-((2-[D$_3$]methoxy-4-(4-(4-[D$_3$]methylpiperazin-1-yl)piperidin-1-yl)phenyl)amino)pyrimidin-4-yl)amino)phenyl)dimethyl phosphorus oxide (the compound of Formula I-3)

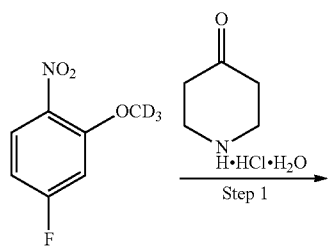

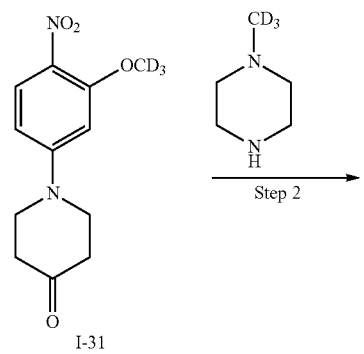

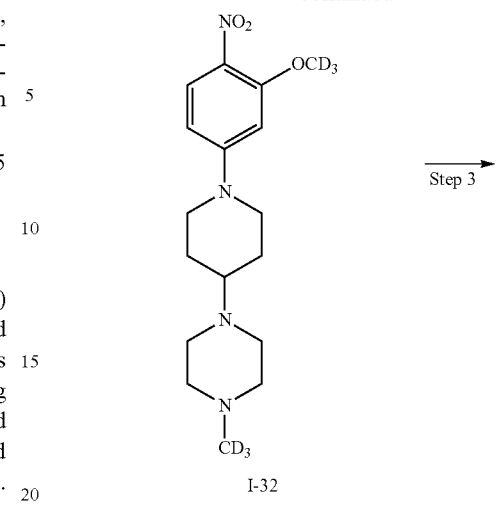

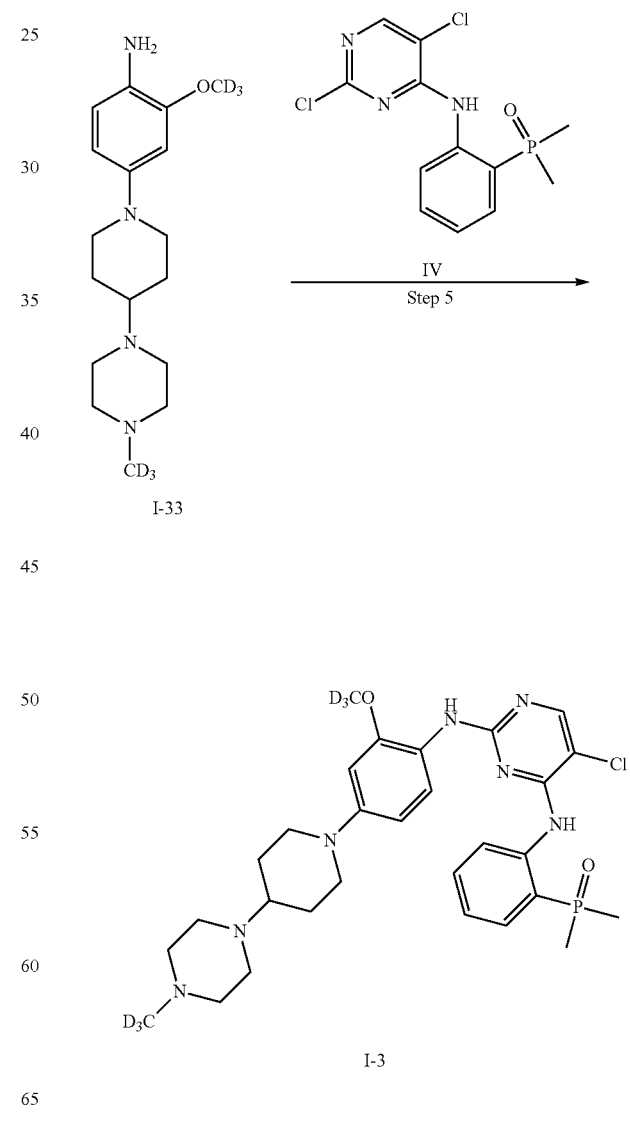

Step 1: Preparation of 1-(3-[D₃]methoxy-4-nitrophenyl)piperidin-4-one (the compound of Formula I-31)

4-fluoro-2-[D₃]methoxy-1-nitrobenzene (3.48 g, 20 mmol), 4-piperidone hydrochloride hydrate (3.38 g, 22 mmol) and anhydrous potassium carbonate (6.91 g, 50 mmol) were dissolved in DMF (50 mL), heated to 75° C. and reacted overnight.

After the reaction was completed, the reaction solution was cooled down to room temperature and filtered by suction. The filter cake was washed with dichloromethane (5 mL×3) and evaporated under reduced pressure to remove the solvent to give a crude product. The crude product was beaten by adding methanol (20 mL), filtered and dried to give 1-(3-[D₃]methoxy-4-nitrophenyl)piperidin-4-one (2.07 g, 40.9% yield), with >98% of D₃ content.

¹H-NMR (300 MHz, CDCl₃): δ=7.99 (d, J=9.2 Hz, 1H), 6.42 (d, J=9.2 Hz, 1H), 6.33 (s, 1H), 3.81-3.77 (m, 4H), 2.65-2.61 (m, 4H).

HRMS (ESI, [M+H]⁺) m/z: 590.2879.

Step 2: Preparation of 1-(1-(3-[D₃]methoxy-4-nitrophenyl)piperidin-4-yl)-4-[D₃]methylpiperazine (the compound of Formula I-32)

As Step 3 in Example 3, 1-(3-[D₃]methoxy-4-nitrophenyl)piperidin-4-one (1.52 g, 6 mmol) reacted with 1-[D₃]methylpiperazine to give 1-(1-(3-[D₃]methoxy-4-nitrophenyl)piperidin-4-yl)-4-[D₃]methylpiperazine (0.6 g, 30.0% yield), with >98% of D₆ content.

¹H-NMR (300 MHz, CDCl₃): δ=8.00 (d, J=9.5 Hz, 1H), 6.43 (dd, J=2.5, 9.5 Hz, 1H), 6.30 (d, J=2.0 Hz, 1H), 3.95 (d, J=13.0 Hz, 2H), 2.98 (t, J=12.0 Hz, 2H), 2.64-2.49 (m, 9H), 1.98 (d, J=12.5 Hz, 2H), 1.66-1.58 (m, 2H).

HRMS (ESI, [M+H]⁺) m/z: 341.2790.

Step 3: Preparation of 2-[D₃]methoxy-4-(4-(4-[D₃]methylpiperazin-1-yl)piperidin-1-yl)aniline (the compound of Formula I-33)

As Step 3 in Example 1, 1-(1-(3-[D₃]methoxy-4-nitrophenyl)piperidin-4-yl)-4-[D₃]methylpiperazine (0.6 g, 1.7 mmol) was reduced to give 2-[D₃]methoxy-4-(4-(4-[D₃]methylpiperazin-1-yl)piperidin-1-yl)aniline (0.5 g), with >98% of D₆ content.

HRMS (ESI, [M+H]⁺) m/z: 311.2704.

Step 4: Preparation of (2-((5-chloro-2-((2-[D₃]methoxy-4-(4-(4-[D₃]methylpiperazin-1-yl)piperidin-1-yl)phenyl)amino)pyrimidin-4-yl)amino)phenyl)dimethyl phosphorus oxide (the compound of Formula I-3)

As Step 4 in Example 1, 2-[D₃]methoxy-4-(4-(4-[D₃]methylpiperazin-1-yl)piperidin-1-yl)aniline reacted with (2-((2,5-dichloropyrimidin-4-yl)amino)phenyl)dimethyl phosphorus oxide to give (2-((5-chloro-2-((2-[D₃]methoxy-4-(4-(4-[D₃]methylpiperazin-1-yl)piperidin-1-yl)phenyl)amino)pyrimidin-4-yl)amino)phenyl)dimethyl phosphorus oxide (0.45 g, 20.7% yield), with >98% of D₆ content.

¹H-NMR (300 MHz, CDCl₃): δ=10.80 (s, 1H), 8.62 (dd, J=4.4, 8.4 Hz, 1H), 8.09-8.08 (m, 2H), 7.47 (dd, J=7.7, 8.0 Hz, 1H), 7.31-7.25 (m, 1H), 7.11 (dd, J=6.5, 6.8 Hz, 1H), 6.54 (d, J=9.2 Hz, 1H), 6.48 (dd, J=1.7, 8.8 Hz, 1H), 3.65 (d, J=12.1 Hz, 2H), 2.77-2.43 (m, 11H), 2.02 (d, J=12.9 Hz, 2H), 1.85, 1.80 (2s, 6H), 1.76-1.72 (m, 2H).

¹³C-NMR (75 MHz, CDCl₃): δ=157.74, 155.86, 154.91, 149.28, 147.35, 143.87, 132.32, 132.29, 129.53, 129.38, 123.09, 123.00, 122.46, 122.29, 122.19, 120.82, 120.56, 119.56, 108.40, 106.01, 101.05, 61.82, 54.79, 50.41, 48.31, 28.08, 19.01, 18.06.

HRMS (ESI, [M+H]⁺) m/z: 590.2879.

EXAMPLE 6

Preparation of (2-((5-chloro-2-((2-methoxy-4-(4-(4-methyl[2,2,6,6-D₄]piperazin-1-yl)piperidine-1-yl)phenyl)amino)pyrimidin-4-yl)amino)phenyl)dimethyl phosphorus oxide (the compound of Formula I-4)

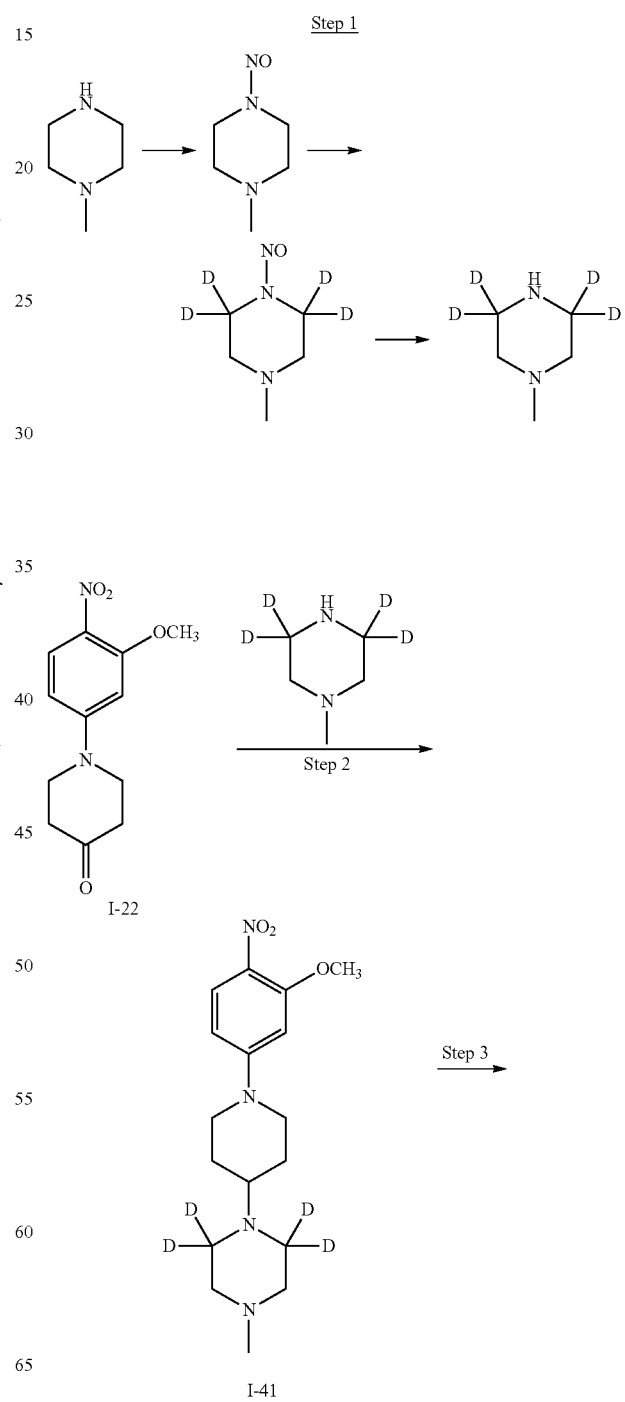

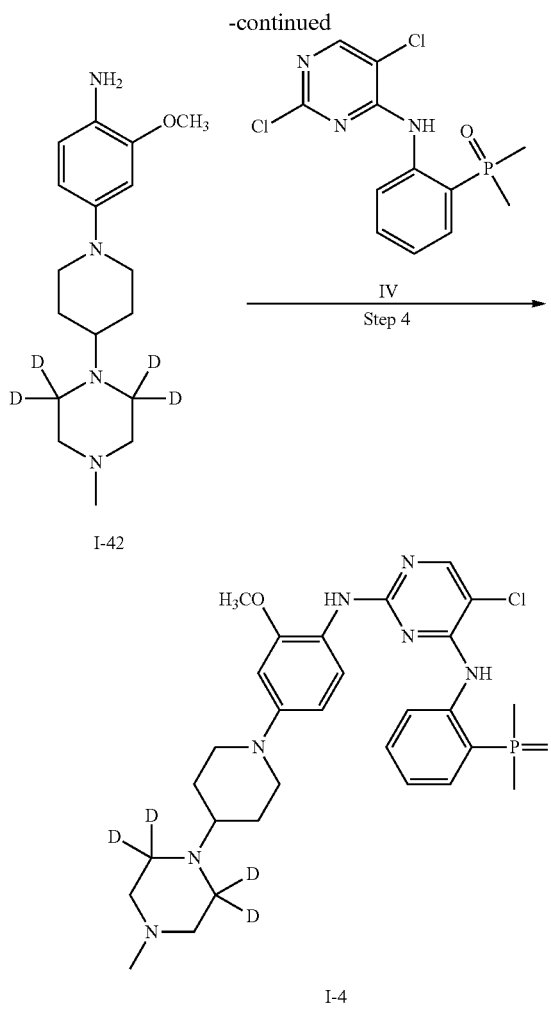

Step 1: Preparation of 1-methyl[3,3,5,5-D₄]piperazine 1-methylpiperazine (20 g, 199.8 mmol) was added in a 250 mL three-necked flask, cooled down to 0° C., slowly added dropwise with 2M hydrochloric acid (233.8 mmol, 111.9 mL) and stirred for 20 minutes. Sodium nitrite (16.27 g, 235.76 mmol) was dissolved in 40 mL water, added dropwise slowly in the three-necked flask at 0° C., stirred at room temperature overnight, and further reacted at 35° C. for 2 hours. After the reaction was completed, the reaction solution was adjusted to alkaline pH using sodium hydroxide, extracted with dichloromethane (100 mL×10), dried over anhydrous sodium sulfate, and evaporated under reduced pressure to remove the solvent, to give 1-methyl-4-nitrosopiperazine (27 g).

Heavy water (425 mL) and sodium methoxide (32.38 g, 599.4 mmol) were added into the above crude product and reacted at 80° C. for 100 hours, concentrated, then extracted with dichloromethane (100 mL×10), dried over anhydrous sodium sulfate, and evaporated under reduced pressure to remove the solvent, to give 1-methyl-nitroso[3,3,5,5-D₄] piperazine (15.68 g).

Heavy water (300 mL) and sodium methoxide (19.68 g, 364.4 mmol) were added into the above crude product and reacted at 80° C. for 40 hours. The reaction solution was then cooled down to 0° C. and added portionwise with Al—Ni alloy (76.30 g) in batches, and the reaction was initiated at room temperature and performed overnight at 0° C. After the reaction was completed, the reaction solution was filtered by suction and the mother liquid was distilled under reduced pressure. The obtained fractions were adjusted to be acidic by using hydrochloric acid, evaporated under reduced pressure to remove water and beaten with ethanol, to give 1-methyl[3,3,5,5-D₄]piperazine hydrochloride (14.13 g, 40.8% yield). The above hydrochloride (6.0 g, 33.86 mmol), anhydrous sodium methoxide (5.49 g, 101.58 mmol) and anhydrous methanol (60 mL) were added in a 250 mL single-necked flask and heated to reflux for 5 hours. After the reaction was completed, the reaction solution was cooled down to room temperature, filtered by suction and evaporated under reduced pressure to remove the solvent, to give a crude product of 1-methyl[3,3,5,5-D₄]piperazine (3.94 g) with 96% of D₄ content, which was used directly in the next step.

HRMS (ESI, [M+H]⁺) m/z: 105.1327.

Step 2: Preparation of 1-(1-(3-methoxy-4-nitrophenyl) piperidin-4-yl)-4-methyl[2,2,6,6-D₄]piperazine (the compound of Formula I-41)

As Step 3 in Example 3, 1-(3-methoxy-4-nitrophenyl) piperidin-4-one (2.50 g, 10 mmol) reacted with 1-methyl[4,4,5,5-D₄]piperazine (2.12 g, 20 mmol) to give 1-(1-(3-methoxy-4-nitrophenyl)piperidin-4-yl)-4-methyl[2,2,6,6-D₄]piperazine (0.7 g, 20.6% yield), with 96% of D₄ content.

¹H-NMR (300 MHz, CDCl₃): δ=7.97 (d, J=9.5 Hz, 1H), 6.40 (dd, J=2.1, 9.4 Hz, 1H), 6.30 (d, J=2.1 Hz, 1H), 3.94-3.80 (m, 6H), 2.96-2.45 (m, 6H), 2.29 (s, 3H), 1.97 (d, J=12.0 Hz, 2H), 1.67-1.54 (m, 2H).

HRMS (ESI, [M+H]⁺) m/z: 339.2216.

Step 3: Preparation of 2-methoxy-4-(4-(4-methyl[2,2,6,6-D₄]piperazin-1-yl)piperidin-1-yl)aniline (the compound of Formula I-42)

As Step 3 in Example 1, 1-(1-(3-methoxy-4-nitrophenyl) piperidin-4-yl)-4-methyl[2,2,6,6-D₄]piperazine (0.70 g) was reduced by hydrogenation to give 2-methoxy-4-(4-(4-methyl[2,2,6,6-D₄]piperazin-1-yl)piperidin-1-yl)aniline (0.63 g, 98.9% yield), with 96% of D₄ content.

¹H-NMR (300 MHz, CDCl₃): δ=6.62 (d, J=8.3 Hz, 1H), 6.51 (s, 1H), 6.41 (dd, J=1.5, 8.2 Hz, 1H), 3.83 (s, 3H), 3.53-3.49 (m, 3H), 2.65-2.46 (m, 6H), 2.29 (s, 3H), 1.92 (d, J=12.0 Hz, 2H), 1.77-1.64 (m, 2H).

HRMS (ESI, [M+H]⁺) m/z: 309.2585.

Step 4: Preparation of (2-((5-chloro-2-((2-methoxy-4-(4-(4-methyl[2,2,6,6-D₄]piperazin-1-yl) piperidin-1-yl)phenyl) amino)pyrimidin-4-yl)amino)phenyl)dimethyl phosphorus oxide (the compound of Formula I-4)

As Step 4 in Example 1, 2-methoxy-4-(4-(4-methyl[2,2,6,6-D₄]piperazin-1-yl)piperidin-1-yl)aniline (0.6 g, 1.94 mmol) reacted with (2-((2,5-dichloropyrimidin-4-yl)amino) phenyl)dimethyl phosphorus oxide (0.4 g, 1.27 mmol) to give (2-((5-chloro-2-((2-methoxy-4-(4-(4-methyl[2,2,6,6-D₄]piperazin-1-yl) piperidin-1-yl)phenyl)amino)pyrimidin-4-yl)amino)phenyl)dimethyl phosphorus oxide (0.32 g, 42.8% yield), with 96% of D₄ content.

₁H-NMR (300 MHz, CDCl₃): δ=10.79 (s, 1H), 8.62 (dd, J=4.3, 8.3 Hz, 1H), 8.08-8.06 (m, 2H), 7.48(dd, J=7.5, 8.1 Hz, 1H), 7.31-7.24 (m, 1H), 7.11 (dd, J=6.6, 7.2 Hz, 1H), 6.54 (s, 1H), 6.49 (d, J=8.8 Hz, 1H), 3.86 (s, 3H), 3.65 (d, J=12.2 Hz, 2H), 2.73-2.41 (m, 7H), 2.33 (s, 3H), 1.96 (d, J=11.2 Hz, 2H), 1.84, 1.80 (2s, 6H), 1.73-1.69 (m, 2H).

¹³C-NMR (75 MHz, CDCl₃): δ=157.76, 155.87, 154.91, 149.31, 147.48, 143.88, 143.84, 132.31, 132.28, 129.50, 129.35, 123.10, 123.00, 122.43, 122.27, 122.09, 122.06, 120.60, 108.37, 105.97, 101.02, 61.69, 55.59, 55.07, 50.42, 45.85, 28.19, 19.00, 18.05.

HRMS (ESI, [M+H]⁺) m/z: 588.2855.

EXAMPLE 7

Preparation of (2-((5-chloro-2-((2-methoxy-4-(4-(4-methyl[D$_8$]piperazin-1-yl)piperidin-1-yl)phenyl)amino)pyrimidin-4-yl)amino)phenyl)dimethyl phosphorus oxide (the compound of Formula I-6)

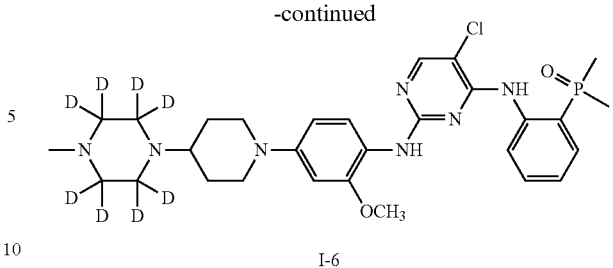

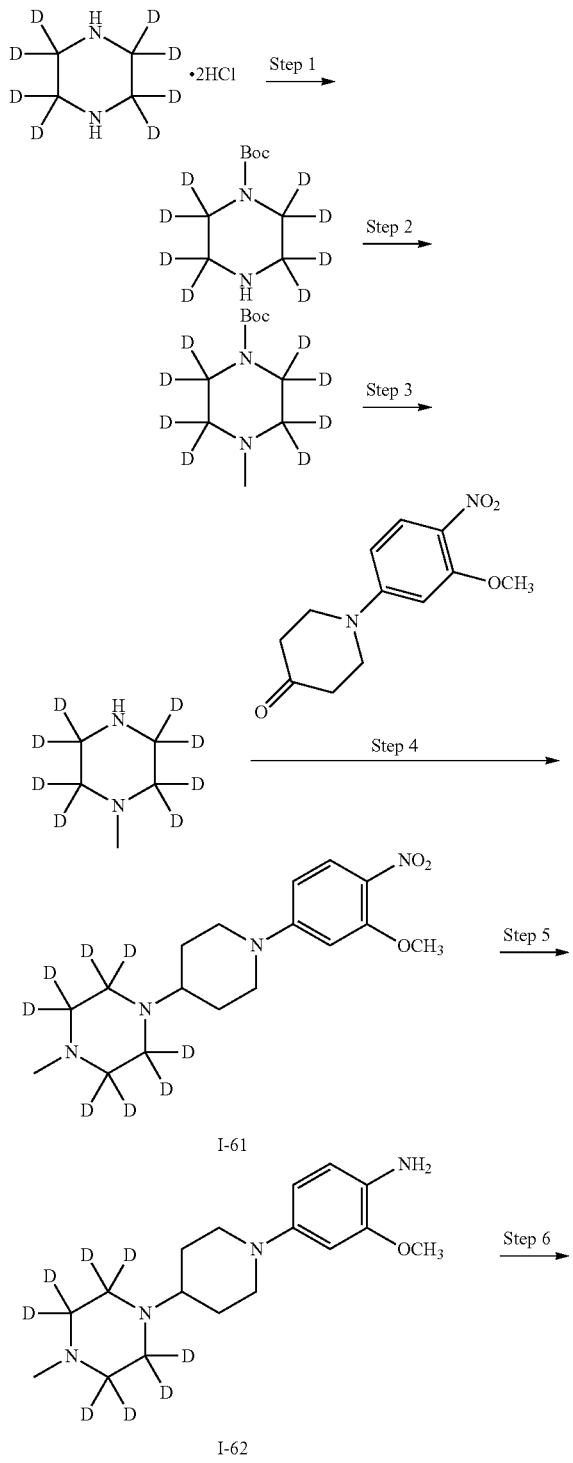

Step 1: Preparation of 1-t-butoxycarbonyl[D$_8$]piperazine

[D$_8$]piperazine hydrochloride (5.0 g, 29.92 mmol), sodium hydroxide (1.3 g, 32.5 mmol), anhydrous methanol (50 mL) were added in a 100 mL single-necked flask and heated to reflux for 3 hours. After the reaction was completed, the reaction solution was cooled down to room temperature and filtered by suction to remove inorganic salts. The filtrate was evaporated to dryness, and the residue was added with water (30 mL) and t-butanol (30 mL), and dissolved completely by stirring. In an ice bath, 2.5N sodium hydroxide solution (30 mL, 75 mmol) was added and a solution of Boc anhydride in t-butanol (20 mL, 14.96 mmol) was then slowly added dropwise, followed by stirring overnight at room temperature. Next day, the reaction solution was evaporated under reduced pressure to remove t-butanol and filtered by suction. The filtrate was extracted with dichloromethane (50 mL×2), dried over anhydrous sodium sulfate, filtered by suction and evaporated under reduced pressure to remove the solvent, to give 1-t-butoxycarbonyl[D$_8$]piperazine (2.6 g, 44.7% yield), with 96% of D$_8$ content.

HRMS ESI, (M+Na) m/z: 195.1944.

Step 2: Preparation of 1-t-butoxycarbonyl-4-methyl[D$_8$]piperazine

In an ice bath, 60% sodium hydrogen (0.64 g, 26.76 mmol) was slowly added portionwise to a solution of 1-t-butoxycarbonyl[D$_8$]piperazine (2.6 g, 13.38 mmol) in tetrahydrofuran (26 mL), and after addition, the ice bath was removed. A solution of methyl p-toluenesulfonate (2.78 g, 14.72 mmol) in tetrahydrofuran (20 mL) was slowly added dropwise, followed by stirring overnight at room temperature. After the reaction was completed, the reaction solution was filtered by suction to give a filter cake. The filter cake was washed with tetrahydrofuran (5 mL×3) and tetrahydrofuran was then removed by evaporation under reduced pressure. The residue was added with water (25 mL), extracted with dichloromethane (25 mL×2), washed with saturated brine (20 mL), dried over anhydrous sodium sulfate, filtered by suction and evaporated under reduced pressure to remove the solvent, to give 1-t-butoxycarbonyl-4-methyl[D$_8$]piperazine (2.26 g, 81% yield), with 96% of D$_8$ content.

Step 3: Preparation of 1-methyl[D$_8$]piperazine 1-t-butoxycarbonyl-4-methyl[D$_8$]piperazine (2.26 g, 10.85 mmol) was dissolved in 10 mL isopropanol, followed by adding an isopropanol hydrochloride solution (5.3 mL, 65.1 mmol) in an ice bath. The reaction solution was warmed up to 50° C. After the reaction was completed, the reaction solution was filtered by suction and the filter cake was dried under vacuum to give 1-methyl[D$_8$]piperazine hydrochloride (1.43 g, 72.7% yield). The hydrochloride was then treated with potassium carbonate to give 1-methyl[D$_8$]piperazine in the free form, with 96% of D$_8$ content.

¹H-NMR (500 MHz, D2O): δ=2.96 (s, 3H), 1.08-1.09 (d, J=6.0 Hz, 1H).
HRMS (ESI, [M+H]⁺) m/z: 109.1679.

Step 4: Preparation of 1-(1-(3-methoxy-4-nitrophenyl)piperidin-4-yl)-4-methyl[D₈]piperazine (the compound of Formula I-61)

As Step 3 in Example 3, 1-(1-(3-methoxy-4-nitrophenyl)piperidin-4-yl)-4-methyl[D₈]piperazine (0.78 g, 22% yield) with 96% of D₈ content was obtained.

¹H-NMR (500 MHz, CDCl₃): δ=8.00 (d, J=9.5 Hz, 1H), 6.42 (dd, J=2.0, 9.5 Hz, 1H), 6.31 (d, J=2.0 Hz, 1H), 3.94-3.80 (m, 5H), 2.98 (t, J=12.0 Hz, 2H), 2.53-2.49 (m, 1H), 2.33 (s, 3H), 1.98 (d, J=12.5 Hz, 2H), 1.66-1.58 (m, 2H).
HRMS (ESI, [M+H]⁺) m/z: 343.2577.

Step 5: Preparation of 2-methoxy-4-(4-(4-methyl[D₈]piperazin-1-yl)piperidin-1-yl)aniline (the compound of Formula I-62)

As Step 4 in Example 3, 2-methoxy-4-(4-(4-methyl[D₈]piperazin-1-yl)piperidin-1-yl)aniline (0.54 g, 73.0% yield) with 96% of D₈ content was obtained.

¹H-NMR (500 MHz, CDCl₃): δ=6.65 (d, J=8.0 Hz, 1H), 6.54 (d, J=1.5 Hz, 1H), 6.43 (dd, J=2.0, 8.5 Hz, 1H), 3.85 (s, 3H), 3.53 (d, J=12.0 Hz, 2H), 2.63 (t, J=12 Hz, 2H), 2.61-2.33 (s, m, 1H), 2.32 (s, 3H), 1.94 (d, J=12.0 Hz, 2H), 1.77-1.69 (m, 2H).
HRMS (ESI, [M+H]⁺) m/z: 313.2829.

Step 6: Preparation of (2-((5-chloro-2-((2-methoxy-4-(4-(4-methyl[D₈]piperazin-1-yl)piperidin-1-yl)phenyl)amino)pyrimidin-4-yl)amino)phenyl)dimethyl phosphorus oxide (the compound of Formula I-6)

As Step 4 in Example 1, (2-((5-chloro-2-((2-methoxy-4-(4-(4-methyl[D₈]piperazin-1-yl)piperidin-1-yl)phenyl)amino)pyrimidin-4-yl)amino)phenyl)dimethyl phosphorus oxide (0.18 g, 26.7% yield) with 92.3% of D₈ content was obtained.

1H-NMR (500 MHz, CDCl₃): δ=10.82 (s, 1H), 8.64 (dd, J=4.5, 8.0 Hz, 1H), 8.11 (s, 1H), 8.10 (s, 1H), 7.51 (dd, J=7.5, 8.1 Hz, 1H), 7.32-7.27 (m, 1H), 7.14 (d, J=1.5 Hz, 1H), 6.56 (d, J=2.5 Hz, 1H), 6.50 (dd, J=2.5, 8.5 Hz, 1H), 3.88 (s, 3H), 3.67 (d, J=12.0 Hz, 2H), 2.72 (t, J=10.0 Hz, 2H), 2.77-2.69 (m, 1H), 2.38 (s, 3H), 1.98 (d, J=12.0 Hz, 2H), 1.86, 1.84 (2s, 6H), 1.78-1.73 (m, 2H).
¹³C-NMR (125 MHz, CDCl₃): δ=157.78, 155.91, 154.97, 149.32, 147.45, 143.93, 132.37, 129.55, 129.46, 123.12, 122.46, 122.36, 122.20, 120.58, 119.83, 108.45, 106.06, 101.11, 61.80, 55.64, 50.50, 45.66, 28.20, 18.88, 18.31.
HRMS (ESI, [M+H]⁺) m/z: 592.3148.

EXAMPLE 8

Preparation of (2-((5-chloro-2-((2-methoxy-4-(4-(4-[D₃]methyl[3,3,5,5-D₄]piperazin-1-yl))piperidin-1-yl)phenyl)amino)pyrimidin-4-yl)amino)phenyl)dimethyl phosphorus oxide (the compound of Formula I-7)

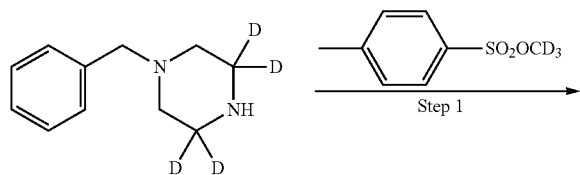

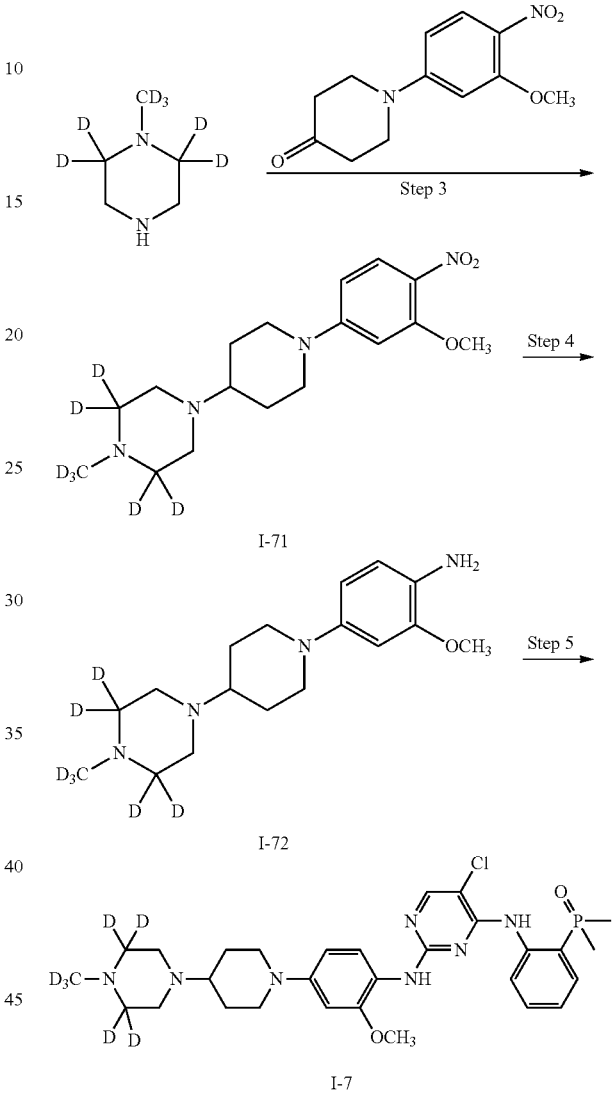

Step 1: Preparation of 1-benzyl-4-[D₃]methylpiperazine
As Step 1 in Example 4, 1-benzyl-4-[D₃]methyl[3,3,5,5-D₄]piperazine (4.6 g, 34.9% yield) with 93.1% of D₇ content was obtained.

Step 2: Preparation of 1-[D₃]methyl[3,3,5,5-D₄]piperazine
As Step 2 in Example 4, 1-[D₃]methyl[3,3,5,5-D₄]piperazine (2.49 g, 100% yield) with 93% of D₇ content was obtained.
HRMS (ESI, [M+H]⁺) m/z: 108.1540.

Step 3: Preparation of 1-(1-(3-methoxy-4-nitrophenyl)piperidin-4-yl)-4-[D₃]methyl[3,3,5,5-D₄]piperazine (the compound of Formula I-71)

As Step 3 in Example 3, 1-(1-(3-methoxy-4-nitrophenyl)piperidin-4-yl)-4-[D₃]methyl[3,3,5,5-D₄]piperazine (0.94 g, 24.1% yield) with 93% of D₇ content was obtained.

¹H-NMR (500 MHz, CDCl₃): δ=7.99 (d, J=9.5 Hz, 1H), 6.41 (dd, J=2.0, 9.5 Hz, 1H), 6.30 (d, J=2.5 Hz, 1H), 3.94-3.93 (m, 5H), 2.98 (td, J=2.0, 12.5 Hz, 2H), 2.64-2.47 (m, 5H), 1.97 (d, J=12.5 Hz, 2H), 1.62 (qd, J=3.5, 12 Hz, 2H).

HRMS (ESI, [M+H]$^+$) m/z: 342.2526.

Step 4: Preparation of 2-methoxy-4-(4-(4-[D$_3$]methyl[3,3,5,5-D$_4$]piperazin-1-yl)piperidin-1-yl)aniline (the compound of Formula I-72)

As Step 4 in Example 3, 2-methoxy-4-(4-(4-[D$_3$]methyl[3,3,5,5-D$_4$]piperazin-1-yl)piperidin-1-yl)aniline (0.85 g, 98.8% yield) with 93% of D$_7$ content was obtained.

$^1$H-NMR (500 MHz, CDCl$_3$): δ=6.63 (d, J=8.5 Hz, 1H), 6.53 (d, J=1.5 Hz, 1H), 6.42 (dd, J=2.5, 8.0 Hz, 1H), 3.83 (s, 3H), 3.52 (d, J=12.5 Hz, 2H), 2.64-2.59 (m, 7H), 1.93 (d, J=12.5 Hz, 2H), 1.72 (qd, J=3.5, 2H).

HRMS (ESI, [M+H]$^+$) m/z: 312.2780.

Step 5: Preparation of (2-((5-chloro-2-((2-methoxy-4-(4-(4-[D$_3$]methyl[3,3,5,5-D$_4$]piperazin-1-yl))piperidin-1-yl)phenyl)amino)pyrimidin-4-yl)amino)phenyl)dimethyl phosphorus oxide (the compound of Formula I-7)

As Step 4 in Example 1, (2-((5-chloro-2-((2-methoxy-4-(4-(4-[D$_3$]methyl[3,3,5,5-D$_4$]piperazin-1-yl))piperidin-1-yl)phenyl)amino)pyrimidin-4-yl)amino)phenyl)dimethyl phosphorus oxide (0.28 g, 28.7% yield) with 93% of D$_7$ content was obtained.

H-NMR (500 MHz, CDCl$_3$): δ=10.82 (s, 1H), 8.64 (dd, J=4.5, 8.5 Hz, 1H), 8.11-8.10 (m, 2H), 7.51 (dd, J=7.5, 8.5 Hz, 1H), 7.32-7.27 (m, 2H), 7.14 (td, J=2.0, 7.0 Hz, 1H), 6.56 (d, J=2.0 Hz, 1H), 6.50 (dd, J=2.0, 8.5 Hz, 1H), 3.88 (s, 3H), 3.67 (d, J=12.0 Hz, 2H), 2.76-2.69 (m, 6H), 2.47-2.44 (m, 1H), 1.99 (d, J=12.5 Hz, 2H), 1.86, 1.84 (2s, 6H), 1.75 (qd, J=3.5, 12.5 Hz, 2H).

13C-NMR (125 MHz, CDCl$_3$): δ=157.77, 155.91, 154.94, 149.31, 147.41, 143.92, 132.37, 129.56, 129.47, 123.06, 122.47, 122.37, 122.23, 120.56, 119.82, 108.46, 106.07, 101.11, 61.86, 55.64, 50.49, 48.25, 28.16, 18.88, 18.31.

HRMS (ESI, [M+H]$^+$) m/z: 591.301.

EXAMPLE 9

Preparation of (2-((5-chloro-2-((2-methoxy-4-(4-(4-methyl[3,3,5,5-D$_4$]piperazin-1-yl)piperidin-1-yl)phenyl)amino)pyrimidin-4-yl)amino)phenyl)dimethyl phosphorus oxide (the compound of Formula I-9)

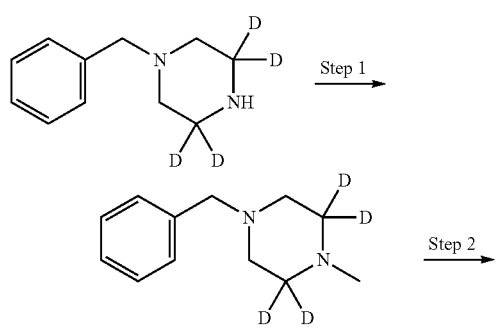

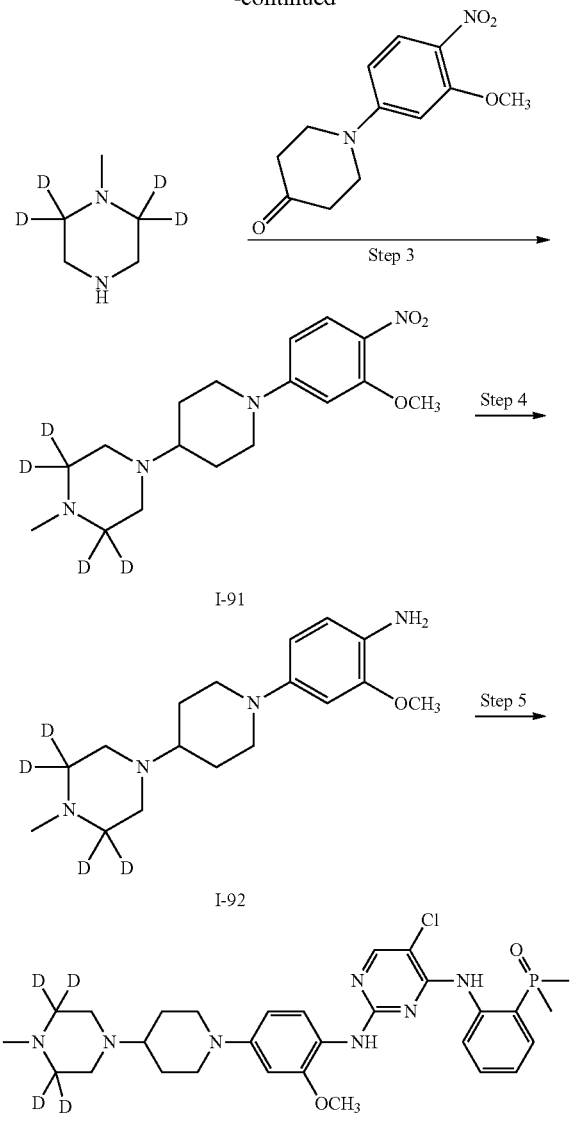

Step 1: Preparation of 1-benzyl-4-[3,3,5,5-D$_4$]piperazine

In an ice bath, 1-phenyl[3,3,5,5-D$_4$]piperazine (15.0 g, 83.20 mmol) was slowly added dropwise to a mixed solution of formic acid (15.6 g, 332.80 mmol) and 37% formaldehyde solution (13.5 g, 166.40 mmol), and then warmed up to reflux. After the reaction was completed, the excess of formic acid in the reaction solution was removed by evaporation under reduced pressure. The residual liquid was adjusted with 10% NaOH aqueous solution to be alkaline. Extraction with dichloromethane (75 mL×2) was performed and the organic phase was washed with saturated brine (50 mL×2), dried over anhydrous sodium sulfate, filtered by suction and evaporated under reduced pressure to remove the solvent, to give a crude product of 16 g. 1-benzyl-4-[3,3,5,5-D$_4$]piperazine (14 g, 87.5% yield) with 96% of D$_4$ content was obtained by column chromatography (dichloromethane:methanol=20:1).

HRMS (ESI, [M+H]$^+$) m/z: 195.1789.

Step 2: Preparation of 1-methyl[3,3,5,5-D$_4$]piperazine 1-benzyl-4-[3,3,5,5-D$_4$]piperazine (11.2 g, 57.6 mmol) was dissolved in anhydrous methanol (45 mL), added with 10% Pd/C (2.2 g) and heated to 50° C., allowing hydrogenation reaction to be performed. After the reaction was completed, the reaction solution was cooled down to room temperature and filtered by suction, and the filtrate was evaporated under atmospheric pressure to remove methanol, to give 1-methyl[3,3,5,5-$D_4$]piperazine (5.8 g, 96.8% yield) with 96% of $D_4$ content.

HRMS (ESI, [M+H]$^+$) m/z: 105.1312.

Step 3: Preparation of 1-(1-(3-methoxy-4-nitrophenyl)piperidin-4-yl)-4-methyl[3,3,5,5-$D_4$]piperazine (the compound of Formula I-91)

1-(3-methoxy-4-nitrophenyl)piperidin-4-one (2.40 g, 9.59 mmol), 1-methyl[3,3,5,5-$D_4$]piperazine (2.00 g, 19.20 mmol), acetonitrile (10 mL), trimethyl orthoformate (2.00 g, 18.82 mmol) and formic acid (1.98 g, 43.02 mmol) were respectively added in a 35 mL pressure tubing, and the mixture was heated in a microwave to 110° C. and reacted for 90 minutes. After the reaction was completed, the reaction solution was cooled down to room temperature, added with water (60 mL) and extracted with ethyl acetate (50 mL×2). The aqueous layer was adjusted to an alkaline pH by using 10% NaOH aqueous solution, extracted with dichloromethane (60 mL×2), washed with saturated brine (50 mL), dried over anhydrous sodium sulfate, and evaporated under reduced pressure to remove the solvent to give a crude product. After adding petroleum ether (10 mL), the crude product was beaten and filtered by suction to give 1-(1-(3-methoxy-4-nitrophenyl)piperidin-4-yl)-4-methyl[3,3,5,5-$D_4$]piperazine (1.42 g, 43.7% yield) with 96% of $D_4$ content.

$^1$H-NMR (500 MHz, CDCl$_3$): δ=7.99 (d, J=9.5 Hz, 1H), 6.42 (dd, J=2.5, 9.5 Hz, 1H), 6.31 (d, J=2.5 Hz, 1H), 3.95-3.94 (m, 5H), 2.98 (td, J=2.5, 12.5 Hz, 2H), 2.61-2.47 (m, 5H), 2.29 (s, 3H), 1.98 (d, J=12.5 HZ, 2H), 1.63 (qd, J=3.5, 12.5 Hz, 2H).

HRMS (ESI, [M+H]$^+$) m/z: 339.2344.

Step 4: Preparation of 2-methoxy-4-(4-(4-methyl[3,3,5,5-$D_4$]piperazin-1-yl)piperidin-1-yl)aniline (the compound of Formula I-92)

As Step 4 in Example 3, 2-methoxy-4-(4-(4-methyl[3,3,5,5-$D_4$]piperazin-1-yl)piperidin-1-yl)aniline (1.1 g, 82% yield) with 96% of $D_4$ content was obtained.

$^1$H-NMR (500 MHz, CDCl$_3$): δ=6.65 (d, J=8.5 Hz, 1H), 6.54 (s, 1H), 6.43 (d, J=7.0 Hz, 1H), 3.85 (s, 3H), 3.53 (d, J=12 Hz, 2H), 2.65-2.36 (m, 7H), 2.31 (s, 3H), 1.94 (d, J=10.5 Hz, 2H), 1.74-1.1.72 (m, 2H).

HRMS (ESI, [M+H]$^+$) m/z: 309.2628.

Step 5: Preparation of (2-((5-chloro-2-((2-methoxy-4-(4-(4-methyl[3,3,5,5-$D_4$]piperazin-1-yl)piperidin-1-yl)phenyl)amino)pyrimidin-4-yl)amino)phenyl)dimethyl phosphorus oxide (the compound of Formula I-9)

As Step 4 in Example 1, (2-((5-chloro-2-((2-methoxy-4-(4-(4-methyl[3,3,5,5-$D_4$]piperazin-1-yl)piperidin-1-yl)phenyl)amino)pyrimidin-4-yl)amino)phenyl)dimethyl phosphorus oxide (0.13 g, 35.13% yield) with 95.4% of $D_4$ content was obtained.

$^1$H-NMR (500 MHz, CDCl$_3$): δ=10.79 (s, 1H), 8.63 (dd, J=4.5, 8.5 Hz, 1H), 8.10-8.09 (m, 2H), 7.50 (dd, J=8.0, 8.0 Hz, 1H), 7.31-7.25 (m, 2H), 7.14 (dd, J=1.0, 7.0 Hz, 1H), 6.56 (d, J=2.0 Hz, 1H), 6.50 (dd, J=2.0, 8.5 Hz, 1H), 3.87 (s, 3H), 3.66 (d, J=12.0 Hz, 2H), 2.75-2.68 (m, 6H), 2.48-2.43 (m, 1H), 2.40 (s, 3H), 1.98 (d, J=12.0 Hz, 2H), 1.85, 1.83 (2s, 6H), 1.75 (qd, J=3.5, 12 Hz, 2H).

$^{13}$C-NMR (125 MHz, CDCl$_3$): δ=157.77, 155.90, 154.94, 149.33, 147.42, 143.85, 132.38, 129.56, 129.47, 123.12, 123.07, 122.50, 122.41, 122.21, 120.60, 119.83, 108.46, 106.03, 101.12, 61.84, 55.65, 50.49, 48.27, 45.46, 28.14, 18.85, 18.28.

HRMS (ESI, [M+H]$^+$) m/z: 588.2936.

EFFECT EXAMPLE 1

Evaluation of Stability of Liver Microsome In Vitro

300 μL of a final incubation system contains 30 μL of monkey liver microsomes (protein concentration: 0.5 mg/mL, American BD Company), 30 μL of NADPH+MgCl$_2$, 3 μL of a substrate (a solution of 1 μmol/L test compound in acetonitrile) and 237 μL of PBS buffer solution. The above incubation system was made in duplicate, each of 0.3 mL.

For each sample, an evenly mixed solution of the substrate and enzyme with a total volume of 270 μL was first prepared, and after pre-incubation at 37° C. for 5 min, 30 μL of NADPH+MgCl$_2$ was added and mixed. 40 μL of the reaction solution was taken respectively at 0, 15, 30, 60 and 90 min, and the reaction was stopped by 300 μL of ice-cold acetonitrile containing an internal standard. In addition, three blanks (KB) were set, each of 300 μL (KB1: no NADPH; KB2: no substrate; KB3: no enzyme).

40 μL of the incubation sample was pipetted out, added with 400 μL of ice-cold acetonitrile containing an internal standard, vortexed for 5 min and centrifuged (13000 rpm, 4° C.) for 10 min. 80 μL of the supernatant was pipetted out in a loading plate, and then 80 μL of 50% acetonitrile aqueous solution was added to the plate and mixed. 1 μL of the mixture was pipetted out for LC/MS/MS assay and the chromatogram was recorded. The results of metabolic stability are shown in Table 1:

TABLE 1

| metabolic stability in monkey liver microsomes | | |
|---|---|---|
| Compounds | $t_{1/2}$ (min) | Prolonging rates |
| Brigatinib | 170 | — |
| I-1 | 229 | 35% |
| I-2 | 236 | 39% |
| I-3 | 199 | 17% |
| I-4 | 176 | 4% |
| I-6 | 223 | 31% |
| I-7 | 227 | 34% |
| I-9 | 214 | 26% |

The compounds of the present invention (especially compounds I-1, I-2, I-6 and I-7) can significantly prolong the half-life period and have more stable metabolism compared to the original drug Brigatinib.

EFFECT EXAMPLE 2

Inhibition Effect on Proliferation In Vitro

1. Experimental Materials
1.1 Cells: human lung cancer cell line NCI—H3122, expressing EML4-ALK fusion protein.
1.2 Main reagents: sulfonyl rhodamine B, RPMI-1640 liquid medium, dimethyl sulfoxide (DMSO), trichloromethane (chloroform).
1.3 Instruments: Varioskan Flash microplate reader.
1.4 Solution preparation: an appropriate amount of a series of test compounds was taken and dissolved using 5% chloroform+95% DMSO, to form a stock solution of 20 mM, which was stored at −20° C. in aliquots. The positive drug Crizotinib was taken and dissolved using 5% chloroform+95% DMSO, and the stock solution was diluted with fresh medium to a working concentration before use. 95 μl DMSO and 5 μl chloroform were taken, mixed together, and diluted with fresh medium to a working concentration before use.

2. Test Methods:

2.1 Cell Culture and Inoculation

The tumor cell line used in tests was cultured in RPM11640 medium containing 10% inactivated Hyclone serum or fetal bovine serum, 100 IU/mL penicillin and 100 IU/mL streptomycin, in a 5% $CO_2$ incubator at 37° C. NCl—H3122 cells were inoculated into a 96-well plate at 5000/well. It was ensured that the cells were in logarithmic growth phase during the whole test.

2.2 Administration

Groups of series of test compounds, negative control and Crizotinib (positive control) were set up in this test. For each test compound group, 6 concentration gradients by 3-fold serial dilution were set, and three wells were for each concentration. For positive control group, 6 concentration gradients by 3-fold serial dilution were set, and three wells were for each concentration. Negative control was 5% chloroform+95% DMSO (the same concentration as that of test compound at 100 nM), and 6 wells were set.

2.3 Sulfonyl rhodamine B method (SRB method)

After the cells were treated with the drugs for 72 hours, the culture medium was discarded. A pre-chilled 10% trichloroacetic acid (TCA) solution was added into each well to fix the cells and the plate was placed in a refrigerator at 4° C. to fix. Each well of the plate was washed with deionized water for 5 times to remove trichloroacetic acid solution. After being dried in air, each well was added with SRB solution (4 mg/ml) prepared with 1% acetic acid and then kept for 20 minutes at room temperature. After the liquid was discarded, each well was washed with 1% acetic acid for 5 times to remove uncombined SRB dye, and then dried in air. An appropriate volume of 10 mM Tris-base (trimethylolamine methane) solution at pH 10.5 was added into each well to dissolve the cells. The plate was shaken on a plate shaker for 10 minutes. The absorbance (OD) value was measured at a wavelength of 490 nm in a microplate reader.

2.4 Result processing

According to the OD values measured by microplate reader, an inhibition rate was calculated as the following formula:

Survival rate (%)=OD of drug well/OD of control well×100%,

If the survival rate was ≥100%, it was recorded as 100%.

Using Calcusyn software, $IC_{50}$ was calculated, and mean and standard deviation thereof were calculated, and the data was expressed as: mean±standard deviation.

3. Test Results:

The results of inhibition effect on proliferation of human lung cancer cell NCl—H3122 were shown in Table 2.

TABLE 2

Inhibition effect on proliferation of human lung cancer cell NCI-H3122

| Compounds | $IC_{50}$ (nM) |
|---|---|
| Brigatinib | 13.29 ± 1.60 |
| I-1 | 10.02 ± 1.05 |
| I-2 | 9.45 ± 1.79 |
| I-3 | 12.68 ± 2.37 |
| I-4 | 11.11 ± 2.07 |
| I-6 | 9.99 ± 2.31 |
| I-7 | 9.89 ± 0.76 |
| I-9 | 7.65 ± 1.07 |
| Crizotinib | 11.05 ± 0.69 |

The results in Table 2 show that the compounds of the present application inhibit the proliferation of human lung cancer cell NCl—H3122 concentration-dependently, and have an excellent inhibitory activity.

What is claimed is:

1. A compound represented by Formula I, or a pharmaceutically acceptable salt, solvate or prodrug thereof,

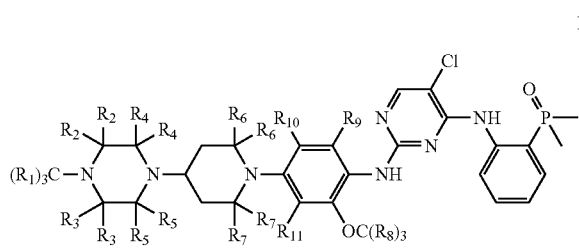

I wherein $R_1$ is selected from deuterium, and $R_2$, $R_3$, $R_4$, $R_5$, $R_6$, $R_7$, $R_8$, $R_9$, $R_{10}$ and $R_{11}$ are each independently selected from hydrogen or deuterium.

2. The compound, or the pharmaceutically acceptable salt, solvate or prodrug thereof according to claim 1, wherein $R_1$ is selected from deuterium, $R_4$, $R_5$, $R_6$, $R_7$, $R_9$, $R_{10}$ and $R_{11}$ are selected from hydrogen and $R_2$, $R_3$ and $R_8$ are each independently selected from hydrogen or deuterium.

3. The compound, or the pharmaceutically acceptable salt, solvate or prodrug thereof according to claim 2, wherein $R_1$ is selected from deuterium, $R_4$, $R_5$, $R_6$, $R_7$, $R_8$, $R_9$, $R_{10}$ and $R_{11}$ are selected from hydrogen and $R_2$ and $R_3$ are each independently selected from hydrogen or deuterium.

4. A compound represented by Formula I, or a pharmaceutically acceptable salt, solvate or prodrug thereof,

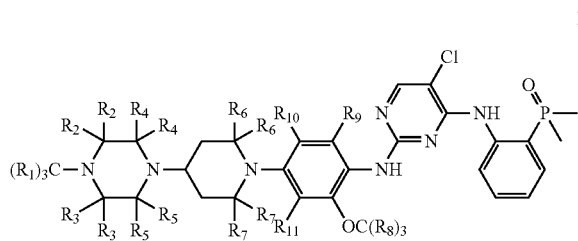

I wherein $R_2$ and $R_3$ are selected from deuterium, and $R_1$, $R_4$, $R_5$, $R_6$, $R_7$, $R_8$, $R_9$, $R_{10}$ and $R_{11}$ are each independently selected from hydrogen or deuterium.

5. The compound, or the pharmaceutically acceptable salt, solvate or prodrug thereof according to claim 4, wherein $R_2$ and $R_3$ are selected from deuterium, $R_6$, $R_7$, $R_8$, $R_9$, $R_{10}$ and $R_{11}$ are selected from hydrogen, and $R_1$, $R_4$ and $R_5$ are each independently selected from hydrogen or deuterium.

6. The compound, or the pharmaceutically acceptable salt, solvate or prodrug thereof according to claim 4, wherein $R_2$ and $R_3$ are selected from deuterium, $R_1$, $R_6$, $R_7$, $R_8$, $R_9$, $R_{10}$ and $R_{11}$ are selected from hydrogen, and $R_4$ and $R_5$ are each independently selected from hydrogen or deuterium.

7. The compound, or the pharmaceutically acceptable salt, solvate or prodrug thereof according to claim 4, wherein $R_1$, $R_2$ and $R_3$ are selected from deuterium, $R_6$, $R_7$, $R_8$, $R_9$, $R_{10}$ and $R_{11}$ are selected from hydrogen, and $R_4$ and $R_5$ are each independently selected from hydrogen or deuterium.

8. A pharmaceutical composition, comprising a therapeutically effective amount of the compound, or a pharmaceutically acceptable salt, solvate or prodrug thereof of claim 1, and one or more pharmaceutically acceptable carriers or excipients.

9. A method of inhibiting anaplastic lymphoma kinase (AKL), comprising administering a therapeutically effective amount of a compound or a pharmaceutically acceptable salt, solvate or prodrug thereof of claim 1 to patients in need thereof.

10. A compound, or a pharmaceutically acceptable salt, solvate or prodrug thereof, wherein the compound is selected from the compounds of the following formulas:

I-1

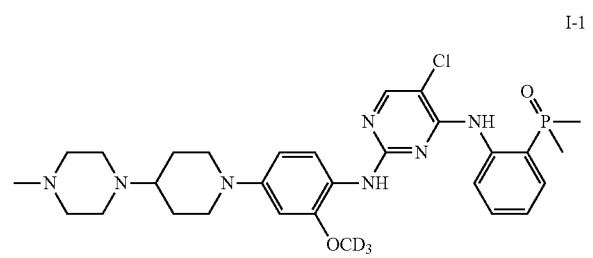

I-2

I-3

I-4

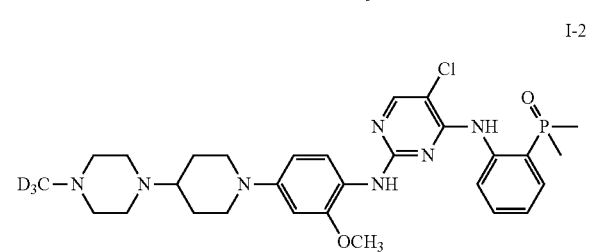

-continued

I-5

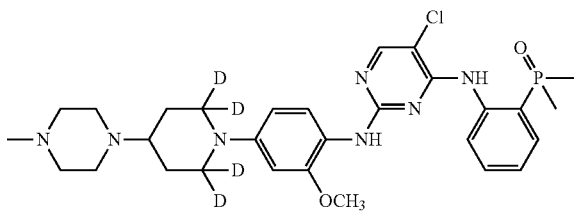

I-6

I-7

I-8

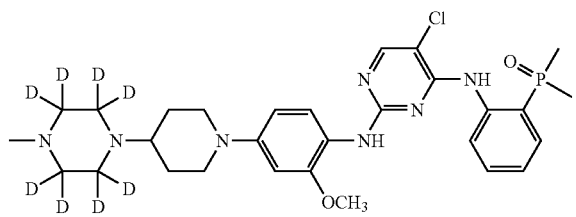

I-9

I-10

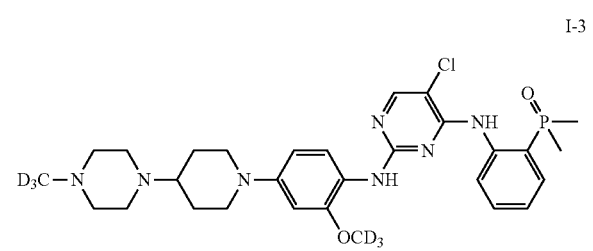

-continued
I-11
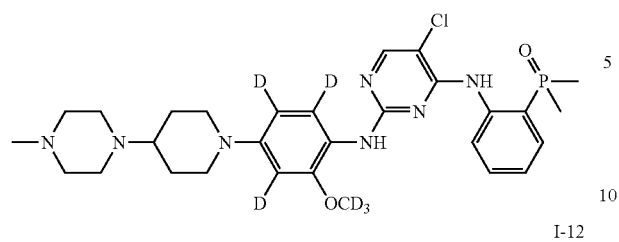
I-12
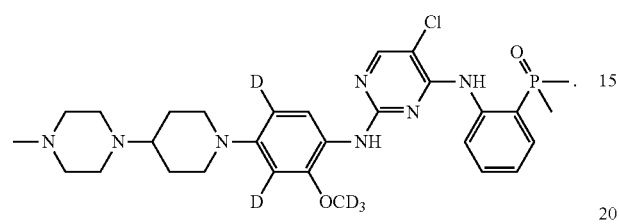
\* \* \* \* \*